(12) United States Patent
Oberhansli et al.

(10) Patent No.: US 12,343,507 B2
(45) Date of Patent: *Jul. 1, 2025

(54) GLASS SYRINGE BARRELS WITH INCREASED CONE BREAKING FORCES

(71) Applicants: Schott Pharma Schweiz AG, St. Gallen (CH); SCHOTT PHARMA AG &CO. KGAA, Mainz (DE)

(72) Inventors: Roman Oberhansli, St. Gallen (CH); Ivo Andreoli, Uzwil (CH); Martha Strassmann, St. Peterzell (CH); Andreas Langsdorf, Ingelheim (DE); Peter Thomas, Koblenz (DE)

(73) Assignees: SCHOTT PHARMA AG & CO. KGAA, Mainz (DE); SCHOTT PHARMA SCHWEIZ AG, St. Gallen (CH)

( * ) Notice: Subject to any disclaimer, the term of this patent is extended or adjusted under 35 U.S.C. 154(b) by 6 days.

This patent is subject to a terminal disclaimer.

(21) Appl. No.: 18/351,186

(22) Filed: Jul. 12, 2023

(65) Prior Publication Data

US 2023/0347061 A1 Nov. 2, 2023

Related U.S. Application Data

(63) Continuation of application No. 16/991,106, filed on Aug. 12, 2020, now Pat. No. 11,833,334.

(30) Foreign Application Priority Data

Aug. 12, 2019 (EP) ..................................... 19191323

(51) Int. Cl.
*A61M 5/31* (2006.01)
*A61J 1/06* (2006.01)
(Continued)

(52) U.S. Cl.
CPC .......... *A61M 5/3129* (2013.01); *A61M 5/315* (2013.01); *A61M 5/3202* (2013.01);
(Continued)

(58) Field of Classification Search
CPC .............. A61M 5/3129; A61M 5/3134; A61M 2205/19; A61M 5/28; A61J 1/065
See application file for complete search history.

(56) References Cited

U.S. PATENT DOCUMENTS

| 4,599,082 A | 7/1986 | Grimard |
| 5,851,201 A | 12/1998 | Ritger |

(Continued)

FOREIGN PATENT DOCUMENTS

| CN | 105362070 | 3/2016 |
| CN | 205215718 | 5/2016 |

(Continued)

OTHER PUBLICATIONS

Section 3.2.1 of the European Pharmacopoeia, 7th edition, 2011.
(Continued)

*Primary Examiner* — Bradley J Osinski
(74) *Attorney, Agent, or Firm* — Ruggiero McAllister & McMahon LLC

(57) ABSTRACT

A glass syringe barrel is provided that has an at least partially conically shaped upper portion and a longitudinal axis. The glass syringe barrel has a top end through which a liquid can be ejected and a bottom end into which a plunger stopper can be pushed. The glass syringe barrel includes, in a direction from the top end to the bottom end, a cone, a shoulder region, and a body region. The shoulder region has and outer contour that has a concave and substantially circular arc-shaped area $c_1$ with an outer radius $r_1$. The outer contour of the glass syringe barrel in the shoulder region is defined by a certain value for $r_1$.

21 Claims, 13 Drawing Sheets

(51) Int. Cl.
*A61M 5/315* (2006.01)
*A61M 5/32* (2006.01)

(52) U.S. Cl.
CPC ............ *A61J 1/065* (2013.01); *A61M 5/3134* (2013.01); *A61M 2205/19* (2013.01)

(56) References Cited

U.S. PATENT DOCUMENTS

| | | | |
|---|---|---|---|
| 7,776,018 | B2 | 8/2010 | Bush |
| 9,017,291 | B2 | 4/2015 | Delabie |
| 10,961,011 | B2 | 3/2021 | Gutekunst |
| 2005/0251096 | A1 | 11/2005 | Armstrong |
| 2009/0171322 | A1* | 7/2009 | Kurimoto ............ A61M 39/10 285/332 |
| 2014/0249479 | A1 | 9/2014 | Pfrang |
| 2015/0322236 | A1 | 11/2015 | Santucci-Aribert |
| 2015/0322366 | A1 | 11/2015 | Santucci-Aribert |
| 2020/0101238 | A1 | 4/2020 | Auerbach |
| 2021/0085878 | A1 | 3/2021 | Oberhansli |

FOREIGN PATENT DOCUMENTS

| | | |
|---|---|---|
| CN | 214232324 | 9/2021 |
| DE | 102009031689 | 12/2010 |
| DE | 102017112823 | 12/2018 |
| EP | 1809353 | 4/2012 |
| JP | 2015073635 | 4/2015 |

OTHER PUBLICATIONS

ISO 11040-4, "Prefilled syringes—Part 4: Glass barrels for injectables and sterilized subassembled syringes ready for filling", Third Edition, Apr. 1, 2015.
Gerresheimer, "Gx® syringe systems and glass cartridges", www.gerresheimer.com; 2018.
Gerresheimer, Product Specification Nov. 15, 2011, 35 pages.
ISO 11040-4, "Prefilled syringes—Part 4: Glass barrels for injectables", Second Edition, Feb. 1, 2007.

* cited by examiner

GLASS SYRINGE BARRELS WITH INCREASED CONE BREAKING FORCES

CROSS REFERENCE TO RELATED APPLICATIONS

This application is a continuation of U.S. application Ser. No. 16/991,106 filed Aug. 12, 2020, which claims benefit under 35 USC § 119 of European Application 19191323.5 filed Aug. 12, 2019, the entire contents of all of which are incorporated herein by reference.

BACKGROUND

1. Field of the Invention

The present invention relates to a glass syringe barrel with an at least partially conically shaped upper portion and having a longitudinal axis $L_{barrel}$, the glass syringe barrel comprising a top end through which a liquid can be ejected and a bottom end into which a plunger stopper can be pushed, the glass syringe barrel comprising in a direction from the top end to the bottom i) a cone region, ii) a shoulder region and iii) a body region. The present invention also relates to a plurality of glass syringe barrels and to a syringe that comprises a glass syringe barrel.

2. Description of Related Art

In order to guarantee a reliable use of pharmaceutical products, pre-filled one-time-use syringes are available commercially. They permit a rapid injection of the product that they contain after a comparatively simple manipulation or handling. This sort of pre-filled syringe has a syringe barrel made from glass or polymer with a syringe head formed on it, in which either a syringe needle is integrated or which has a Luer connecting cone of a conical connection, if necessary, a lockable cone connection (Luer lock). A grip plate is mounted on the other open end of the syringe barrel, either formed in one piece with it or put on it as a separate part. An elastomeric piston stopper is slidable through the open end of the syringe barrel. The piston stopper has a threaded blind hole, in which a piston rod with a threaded front end is screwable in various embodiments. The aforementioned single-use syringe, also called a ready-made syringe, with a syringe barrel made of glass, is described in Norm DIN ISO 11040, in which, for example, the syringe barrel is described in part 4. The elastomeric standard piston stopper and standard piston rod made of polymer with a cruciform cross section are described in part 5.

There are two varieties of Luer taper connections: locking and slipping. "Luer-Lock" style connectors are often generically referred to as "Luer-lock", and "Luer-slip" style connectors may be generically referred to as "slip tip". Luer-lock fittings are securely joined by means of a tabbed hub on the female fitting which screws into threads in a sleeve on the male fitting. Slip tip (Luer-slip) fittings simply conform to Luer taper dimensions and are pressed together and held by friction (they have no threads). A glass syringe designed for a Luer-lock style connector usually is characterized in that it comprises an upper portion that is at least partially conically shaped over which the Luer components are pushed, usually followed by a constriction region in which the diameter is reduced compared to the diameter of the cone region. The reduced diameter in the constriction region creates a notch around the conically shaped upper portion, which allows the Luer-lock adapter (which is a sleeve made of plastic that comprises the threads) to "snap in" and thus securely hold these components on the syringe.

In a glass syringe barrel comprising designed for a Luer-lock style connector or for a Luer-slip style connector the outer diameter of the conically upper portion is only about 4 mm with a wall thickness of the glass in the cone region of only about 1 to about 2 mm. Accordingly, such glass syringe barrels are very susceptible to mechanical stresses in the cone region, such as those mechanical stresses which occur when a Luer adapter is attached to the conically shaped upper portion, when a needle in a Luer adapter that is attached to the Luer cone is inserted into human or animal tissue as part of the intended use of such a syringe, or when such glass syringe barrels are transported in a packaging unit that contains large number of such syringes packaged in a confined space.

SUMMARY

In general, it is an object of the present invention to at least partly overcome a disadvantage arising from the prior art. It is a further object of the present invention to provide a glass syringe barrel comprising an at least partially conically shaped upper portion, particularly a Luer cone designed for a Luer-lock style connector or for a Luer-slip style connector, which, compared to similar glass syringe barrels known from the prior art, has an improved resistance towards pressure that is applied onto the cone region of the glass syringe barrel. It is a further object of the present invention to provide a glass syringe barrel comprising an at least partially conically shaped upper portion, particularly a Luer designed for a Luer-lock style connector or for a Luer-slip style connector, which, compared to similar glass syringe barrels known from the prior art, has an improved resistance towards pressure that is applied onto the cone region of the glass syringe barrel and which has been prepared by a process as simple as possible, preferably from prefabricated glass tubing by shaping and separation. It is a further object of the present invention to provide a process for the preparation of a glass syringe barrel comprising an at least partially conically shaped upper portion, particularly a Luer cone designed for a Luer-lock style connector or for a Luer-slip style connector, which, compared to similar glass syringe barrels known from the prior art, has an improved resistance towards pressure that is applied onto the cone region of the glass syringe from prefabricated glass tubing by shaping and separation, wherein no additional process steps such as a modification of the glass surface or the thickening of the glass in the cone- and/or shoulder region are required.

A contribution to solving at least one of the objects according to the invention is made by an embodiment 1 of a glass syringe barrel with an at least partially conically shaped upper portion, the glass syringe barrel having a longitudinal axis $L_{barrel}$ and comprising a top end through which a liquid can be ejected and a bottom end into which a plunger stopper can be pushed, the glass syringe barrel comprising in a direction from the top end to the bottom end: a cone region having a first end that corresponds to the top end of the glass syringe barrel and a second end, wherein the cone region has a length $l_1$ and an outer diameter $d_1$ at the second end; a shoulder region having a first end that is adjacent to the second end of the cone region and a second end, wherein the outer contour of the shoulder region comprises a concave and substantially circular arc-shaped area $c_1$ with an outer radius $r_1$ beginning below the second end of the cone region and a convex and substantially circular arc-shaped area $c_2$ with an outer radius $r_2$ beginning above the second end of the shoulder region; a body region having a first end that is adjacent to the second end of the shoulder region and a second end that preferably corresponds to the bottom end of the glass syringe barrel, wherein the body region has an outer diameter $d_2$ and a glass thickness $n_2$; wherein $r_1$ is in the range from 0.4 to 3 mm, preferably in the range from 0.5 to 2.5 mm, more preferably in the range from 0.6 to 2 mm, even more preferably in the range from 0.7 to 1.8 mm and most preferably in the range from 0.8 to 1.5 mm. According to a particularly preferred embodiment of the glass syringe barrel according to the invention $r_1$ is in the range from 0.5 to 3 mm.

A contribution to solving at least one of the objects according to the invention is also made by an embodiment 1 of a plurality 1 of glass syringe barrels, each glass syringe barrel having an at least partially conically shaped upper portion and each glass syringe barrel having a longitudinal axis $L_{barrel}$ and comprising a top end through which a liquid can be ejected and a bottom end into which a plunger stopper can be pushed, each glass syringe barrel comprising in a direction from the top end to the bottom end: a cone region having a first end that corresponds to the top end of the glass syringe barrel and a second end, wherein the cone region has a length $l_1$ and an outer diameter $d_1$ at the second end; a shoulder region having a first end that is adjacent to the second end of the cone region and a second end, wherein the outer contour of the shoulder region comprises a concave and substantially circular arc-shaped area $c_1$ with an outer radius $r_1$ beginning below the second end of the cone region and a convex and substantially circular arc-shaped area $c_2$ with an outer radius $r_2$ beginning above the second end of the shoulder region; a body region having a first end that is adjacent to the second end of the shoulder region and a second end that corresponds to the bottom end of the glass syringe barrel, wherein the body region has an outer diameter $d_2$ and a glass thickness $n_2$; wherein for at least 75%, preferably for at least 85%, more preferably for at least 95% and most preferably for each of the glass syringe barrels contained in the plurality 1 of glass syringe barrels $r_1$ is in the range from 0.4 to 3 mm, preferably in the range from 0.5 to 2.5 mm, more preferably in the range from 0.6 to 2 mm, even more preferably in the range from 0.7 to 1.8 mm and most preferably in the range from 0.8 to 1.5 mm.

A contribution to solving at least one of the objects according to the invention is also made by an embodiment 1 of a plurality 2 of glass syringe barrels, each glass syringe barrel having an at least partially conically shaped upper portion and each glass syringe barrel having a longitudinal axis $L_{barrel}$ and comprising a top end through which a liquid can be ejected and a bottom end into which a plunger stopper can be pushed, each glass syringe barrel comprising in a direction from the top end to the bottom end: a cone region having a first end that corresponds to the top end of the glass syringe barrel and a second end, wherein the cone region has a length $l_1$ and an outer diameter $d_1$ at the second end; a shoulder region having a first end that is adjacent to the second end of the cone region and a second end, wherein the outer contour of the shoulder region comprises a concave and substantially circular arc-shaped area $c_1$ with an outer radius $r_1$ beginning below the second end of the cone region and a convex and substantially circular arc-shaped area $c_2$ with an outer radius $r_2$ beginning above the second end of the shoulder region; a body region having a first end that is adjacent to the second end of the shoulder region and a second end that corresponds to the bottom end of the glass syringe barrel, wherein the body region has an outer diameter $d_2$ and a glass thickness $n_2$; wherein for the Luer cone breaking resistance the 1% quantile of the glass syringe barrels contained in the plurality of glass syringe barrels is at least 50 N, preferably at least 65 N, more preferably at least 80 N, even more preferably at least 95 N and most preferably at least 110 N, and/or for the Luer cone breaking resistance the 50% quantile of the glass syringe barrels contained in the plurality of glass syringe barrels is at least 145 N, preferably at least 175 N, more preferably at least 205 N, even more preferably at least 230 N and most preferably at least 270 N.

A plurality of glass syringe barrels has a 1% quantile of 50 N for the Luer cone breaking resistance of at least 1% of the glass syringe barrels have a Luer cone breaking resistance of 50 N or less and of at least 99% of have a Luer cone breaking resistance of 50 N or more. A plurality of glass syringe barrels has a 50% quantile of 145 N for the Luer cone breaking resistance of at least 50% of the glass syringe barrels have a Luer cone breaking resistance of 145 N or less and of at least 50% of have a Luer cone breaking resistance of 145 N or more.

"A plurality of glass syringes" in the sense of the present invention preferably comprises at least 10 glass syringes, preferably at least 25 glass syringes, more preferably at least 50 glass syringes, even more preferably at least 100 glass syringes even more preferably at least 200 glass syringes and most preferably at least 400 glass syringes. Furthermore, the plurality of glass syringes preferably has been collected arbitrarily and particularly has not been selected with regard to any property. For example, the plurality glass syringes may be the group of syringes which are packed together in a typical transport tray.

In an embodiment 2 of the glass syringe barrel 1 according to the invention or of the plurality 1 or 2 of glass syringe barrels according to the invention, the glass syringe barrel 1 or the plurality 1 or 2 of glass syringe barrels is designed according to its embodiment 1, wherein for the glass syringe barrel 1 or for at least 75%, preferably for at least 85%, more preferably for at least 95% and most preferably for each glass syringe barrel contained in the plurality 1 or 2 of glass syringe barrels the following condition are fulfilled: if the glass syringe barrel is placed on a plane horizontal substrate with the outer surface of the body region on it, within any given cross-section of the glass syringe barrel that is located in a plane being centrically located in the glass syringe barrel and comprising the longitudinal axis $L_{barrel}$ of the glass syringe barrel, f(x) defines the vertical distance between the substrate and the outer surface of the glass syringe barrel at a given position x, $k(x)=|f''(x)/[1+f'(x)^2]^{3/2}|$ defines the absolute value of the curvature of f(x) at a given position x, and in the interval between $x=P_1$ and $x=P_2$ for any concave curvature in this interval the minimum value for $(1/k(x))/n_2^2$ is at least 0.5 $mm^{-1}$, preferably at least 0.6 $mm^{-1}$, more preferably at least 0.75 $mm^{-1}$, even more preferably at least 0.85 $mm^{-1}$ and most preferably at least 1.0 $mm^{-1}$, wherein $P_1$ defines the x-position at which the outer diameter of the glass syringe barrel is $0.95 \times d_2$ and $P_2$ is $P_1 + 3 \times n_2$.

In an embodiment 3 of the glass syringe barrel 1 according to the invention or of the plurality 1 or 2 of glass syringe barrels according to the invention, the glass syringe barrel 1 or the plurality 1 or 2 of glass syringe barrels is designed according to its embodiment 2, wherein for the glass syringe barrel 1 or for at least 75%, preferably for at least 85%, more preferably for at least 95% and most preferably for each glass syringe barrel contained in the plurality 1 or 2 of glass syringe barrels in the interval between $x=P_1$ and $x=P_2$ the maximum value of the first derivative $f'(x)_{max}$ of $f(x)$ is less than 18, even more preferably less than 15, even more preferably less than 10 and most preferably less than 5.

In an embodiment 4 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 3, wherein for the glass syringe barrel 1 or for at least 75%, preferably for at least 85%, more preferably for at least 95% and most preferably for each glass syringe barrel contained in the plurality 1 or 2 of glass syringe barrels $r_2$ is in the range from 1.2 to 3.1 mm, preferably in the range from 1.4 to 2.9 mm, more preferably in the range from 1.6 to 2.7 mm, even more preferably in the range from 1.8 to 2.5 mm and most preferably in the range from 2.0 to 2.3 mm.

In an embodiment 5 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 4, wherein the glass syringe barrel further comprises a constriction region that is located between the cone region and the shoulder region, the constriction region having a first end that is adjacent to the second end of the cone region, a second end that is adjacent to the first end of shoulder region and an outer contour $c_3$, wherein the constriction region has a length $l_1'$, a minimum outer diameter $d_1' < d_1$ below the first end of the constriction region and an outer diameter $d_1''$ at the second end of the constriction region.

In an embodiment 6 of the glass syringe barrel 1 according to the invention or of the plurality 1 or 2 of glass syringe barrels according to the invention, the glass syringe barrel 1 or the plurality 1 or 2 of glass syringe barrels is designed according to its embodiment 5, wherein the outer contour $c_3$ of the glass syringe barrel in the constriction region is conically shaped with $d_1' < d_1''$ and wherein at the second end of the constriction region $c_3$ merges into $c_1$ without any offset.

In an embodiment 7 of the glass syringe barrel 1 according to the invention or of the plurality 1 or 2 of glass syringe barrels according to the invention, the glass syringe barrel 1 or the plurality 1 or 2 of glass syringe barrels is designed according to its embodiment 6, wherein in the constriction region a first line that runs parallel to the longitudinal axis $L_{barrel}$ and a second line that runs parallel to $c_3$ and that runs in the same plane as the first line include an angle $\gamma$, and wherein for the glass syringe barrel 1 or for at least 75%, preferably for at least 85%, more preferably for at least 95% and most preferably for each glass syringe barrel contained in the plurality 1 or 2 of glass syringe barrels $\gamma$ is in the range from 0.3 to 2.5°, preferably in the range from 0.5 to 2.0° and most preferably in the range from 0.7 to 1.5°.

In an embodiment 8 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 7, wherein for the glass syringe barrel 1 or for at least 75%, preferably for at least 85%, more preferably for at least 95% and most preferably for each glass syringe barrel contained in the plurality 1 or 2 of glass syringe barrels $l_1$ or, in case of a constriction region, the total length $l_1+l_1'$, is in the range from 8 to 12 mm, preferably in the range from 8.25 to 10.5 mm, more preferably in the range from 8.5 to 10 mm, even more preferably in the range from 8.6 to 9.8 mm, even more preferably in the range from 8.7 to 9.6 mm and most preferably in the range from 9.4 to 9.6 mm.

In an embodiment 9 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 5 to 8, wherein for the glass syringe barrel 1 or for at least 75%, preferably for at least 85%, more preferably for at least 95% and most preferably for each glass syringe barrel contained in the plurality 1 or 2 of glass syringe barrels $l_1'$ is in the range from 1 to 3 mm, preferably in the range from 1.1 to 2.5 mm, more preferably in the range from 1.2 to 2 mm even more preferably in the range from 1.3 to 1.8 mm and most preferably in the range from 1.4 to 1.6 mm.

In an embodiment 10 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 9, wherein for the glass syringe barrel 1 or for at least 75%, preferably for at least 85%, more preferably for at least 95% and most preferably for each glass syringe barrel contained in the plurality 1 or 2 of glass syringe barrels $d_1$ is in the range from 4 to 4.8 mm, preferably in the range from 4.2 to 4.6 mm, more preferably in the range from 4.3 to 4.5 mm, even more preferably in the range from 4.35 to 4.45 mm and most preferably in the range from 4.40 to 4.42 mm. Preferably, $d_1$ is the maximum outer diameter of the cone region. It is furthermore preferred that the second end of the cone region (or, if the cone region comprises a construction region, the second end of the constriction region) preferably corresponds to the point at which the outer diameter $d_1$ exceeds a value of 4.4 mm In an embodiment 11 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 10, wherein for the glass syringe barrel 1 or for at least 75%, preferably for at least 85%, more preferably for at least 95% and most preferably for each glass syringe barrel contained in the plurality 1 or 2 of glass syringe barrels $d_2$ is in the range from 6 to 15 mm, preferably in the range from 6.5 to 14 mm, more preferably in the range from 7 to 13 mm, even more preferably in the range from 7.5 to 12 mm and most preferably in the range from 8 to 11 mm.

In an embodiment 12 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 11, wherein the outer surface of glass syringe barrel in the cone region is roughened or is provided with a coating.

In an embodiment 13 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 5 to 12, wherein for the glass syringe barrel 1 or for at least 75%, preferably for at least 85%, more preferably for at least 95% and most preferably for each glass syringe barrel contained in the plurality 1 or 2 of glass syringe barrels $d_1'$ is in the range from 3.4 to 5.2 mm, preferably in the range from 3.6 to 5 mm, more preferably in the range from 3.8 to 4.8 mm, even more preferably in the range from 4 to 4.6 mm and most preferably in the range from 4.2 to 4.4 mm.

In an embodiment 14 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 5 to 13, wherein in the glass syringe barrel 1 or in at least 75%, preferably for at least 85%, more preferably for at least 95% and most preferably in each glass syringe barrel contained in the plurality 1 or 2 of glass syringe barrels, the maximum thickness of the glass in the constriction region is in the range from 1.3 to 2.1 mm, preferably in the range from 1.4 to 2 mm, more preferably in the range from 1.5 to 1.9 mm, even more preferably in the range from 1.6 to 1.8 mm and most preferably in the range from 1.65 to 1.75 mm.

In an embodiment 15 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 5 to 14, wherein in the glass syringe barrel 1 or in at least 75%, preferably for at least 85%, more preferably for at least 95% and most preferably in each glass syringe barrel contained in the plurality 1 or 2 of glass syringe barrels the minimum thickness of the glass in the constriction region is in the range from 1.1 to 1.9 mm, preferably in the range from 1.2 to 1.8 mm, more preferably in the range from 1.3 to 1.7 mm, even more preferably in the range from 1.4 to 1.6 mm and most preferably in the range from 1.45 to 1.55 mm.

In an embodiment 16 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 15, wherein in the glass syringe barrel 1 or in at least 75%, preferably for at least 85%, more preferably for at least 95% and most preferably in each glass syringe barrel contained in the plurality 1 or 2 of glass syringe barrels the shoulder region is characterized by an outer shoulder angle $\alpha$ in the range from 6 to 28°, preferably in the range from 8 to 22°, more preferably in the range from 9 to 16°, even more preferably in the range from 10 to 15° and most preferably in the range from 11 to 14.

In an embodiment 17 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 16, wherein in the glass syringe barrel 1 or in at least 75%, preferably for at least 85%, more preferably for at least 95% and most preferably in each glass syringe barrel contained in the plurality 1 or 2 of glass syringe barrels the shoulder region is characterized by an inner shoulder angle $\beta$ in the range from 22 to 50° preferably in the range from 25 to 40°, more preferably in the range from 26 to 35°, even more preferably in the range from 27 to 32° and most preferably in the range from 28 to 31°.

In an embodiment 18 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 17, wherein $n_s$ is the glass thickness in the shoulder region, measured at the point of the inner shoulder surface at which the surface for the first time forms an angle of 30° with longitudinal axis $L_{barrel}$, and wherein in the glass syringe barrel 1 or in at least 75%, preferably for at least 85%, more preferably for at least 95% and most preferably in each glass syringe barrel contained in the plurality 1 or 2 of glass syringe barrels $n_s$ is in the range from 1.2 to 2 mm, preferably in the range from 1.3 to 1.8 mm, more preferably in the range from 1.3 to 1.6 mm, even more preferably in the range from 1.35 to 1.5 mm and most preferably in the range from 1.35 to 1.45 mm.

In an embodiment 19 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 18, wherein 12 is the length of the body region and wherein in the glass syringe barrel 1 or in at least 75%, preferably for at least 85%, more preferably for at least 95% and most preferably in each glass syringe barrel contained in the plurality 1 or 2 of glass syringe barrels 12 is in the range from 30 to 60 mm, preferably in the range from 35 to 55 mm, more preferably in the range from 38 to 50 mm, even more preferably in the range from 39.5 to 45 mm and most preferably in the range from 39.5 to 41 mm.

In an embodiment 20 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 19, wherein in the glass syringe barrel 1 or in at least 75%, preferably for at least 85%, more preferably for at least 95% and most preferably in each glass syringe barrel contained in the plurality 1 or 2 of glass syringe barrels $n_2$ is in the range from 0.6 to 1.6 mm, preferably in the range from 0.7 to 1.5 mm, more preferably in the range from 0.8 to 1.4 mm, even more preferably in the range from 0.9 to 1.3 mm and most preferably in the range from 1 to 1.2 mm.

In an embodiment 21 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 20, wherein the glass syringe barrel has a nominal volume V and wherein in the glass syringe barrel 1 or in at least 75%, preferably for at least 85%, more preferably for at least 95% and most preferably in each glass syringe barrel contained in the plurality 1 or 2 of glass syringe barrels V in a range from 0.5 to 11 ml, preferably from 0.5 to 9 ml, more preferably from 0.5 to 7 ml, even more preferably from 0.5 to 5 ml, most preferably from 0.5 to 3 ml.

In an embodiment 22 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 21, wherein the glass syringe barrel has a length $l_3$, measured as the distance between the top end and the bottom end, and wherein in the glass syringe barrel 1 or in at least 75%, preferably for at least 85%, more preferably for at least 95% and most preferably in each glass syringe barrel contained in the plurality 1 or 2 of glass syringe barrels 13 in the range from 30 to 100 mm, preferably in the range from 35 to 95 mm, more preferably in the range from 40 to 90 mm, even more preferably in the range from 45 to 86 mm and most preferably in the range from 46 to 70 mm.

In an embodiment 24 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 23, wherein the glass syringe barrel 1 or at least 75%, preferably at least 85%, more preferably at least 95% and most preferably each glass syringe barrel contained in the plurality 1 or 2 of glass syringe barrels is rotation-symmetric around the longitudinal axis $L_{barrel}$ that runs parallel to the body region and that preferably goes through the center of the top end and the bottom end.

In an embodiment 24 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 23, wherein the glass syringe barrel is designed for a Luer-slip style connector and is sealed with a tip cap that is attached to the at least partially conically shaped upper portion.

In an embodiment 25 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 24, wherein the glass syringe barrel is designed for a Luer-lock style connector and comprises a Luer-lock adapter that is attached to the at least partially conically shaped upper portion.

In an embodiment 26 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 25, wherein a needle is attached to the at least partially conically shaped upper portion via a Luer connector and wherein the needle is sealed with a needle cap.

In an embodiment 28 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 27, wherein the syringe further comprises iv) a flange region having a first end that is adjacent to the second end of the body region and a second end that comprises a finger flange and that corresponds to the bottom end of the glass syringe barrel, wherein the flange region has an outer diameter $d_3 > d_2$.

In an embodiment 29 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 28, wherein the glass is of a type selected from the group consisting of is selected from the group consisting of a borosilicate glass, an aluminosilicate glass, soda lime glass and fused silica.

In an embodiment 30 of the glass syringe barrel 1 according to the invention or of the plurality 1 or 2 of glass syringe barrels according to the invention, the glass syringe barrel 1 or the plurality 1 or 2 of glass syringe barrels is designed according to anyone of its embodiments 1 to 29, wherein the glass syringe barrel comprises a coating that at least partially superimposes the interior surface of the body region.

A contribution to solving at least one of the objects according to the invention is made by an embodiment 1 of a process or making an item, preferably a glass syringe barrel, more preferably a glass syringe barrel 1 according to the invention, comprising as process steps: loading a glass tube having a longitudinal axis $L_{tube}$ (that corresponds to $L_{barrel}$ in the finished glass syringe barrel), a first end and a further end into a machine, preferably a rotary machine, the glass tube having a wall thickness $n_2$ and an outer diameter $d_2$; heating the first end of the glass tube, while rotating around its longitudinal axis, to a temperature above its glass transition temperature, preferably above its softening temperature, with a heating element, preferably with a flame; while the glass tube is rotating around its longitudinal axis, shaping the first end that has been heated using one or more molding tools that act on predetermined positions of the outer surface of the glass tube at the first end to form a cone region having a first end that corresponds to the top end of the glass syringe barrel and a second end, wherein the cone region has a length $l_1$ and an outer diameter $d_1$ at the second end; a shoulder region having a first end that is adjacent to the second end of the cone region and a second end, wherein the outer contour of the shoulder region comprises a concave and substantially circular arc-shaped area $c_1$ with an outer radius $r_1$ beginning below the second end of the cone region and a convex and substantially circular arc-shaped area $c_2$ with an outer radius $r_2$ beginning above the second end of the shoulder region; a body region having a first end that is adjacent to the second end of the shoulder region and a second end that preferably corresponds to the bottom end of the glass syringe barrel, wherein the body region has an outer diameter $d_2$ and a glass thickness $n_2$; wherein shaping in process step III) is performed in such a way that $r_1$ is in the range from 0.4 to 3 mm, preferably in the range from 0.5 to 2.5 mm, more preferably in the range from 0.6 to 2 mm, even more preferably in the range from 0.7 to 1.8 mm and most preferably in the range from 0.8 to 1.5 mm.

In an embodiment 3 of the process 1 according to the invention, the process 1 is designed according to its embodiment 1, wherein shaping in process step III) is performed in such a way that an outer counter in the shoulder region is obtained that is characterized by the following features: if the shaped glass tube is placed on a plane horizontal substrate with the outer surface of the body region on it, within any given cross-section of the glass syringe barrel that is located in a plane being centrically located in the glass syringe barrel and comprising the longitudinal axis $L_{tube}$ of the shaped glass tube, f(x) defines the vertical distance between the substrate and the outer surface of the glass syringe barrel at a given position x, $k(x)=|f''(x)/[1+f'(x)^2]^{3/2}|$ defines the absolute value of the curvature of f(x) at a given position x, and in the interval between $x=P_1$ and $x=P_2$ for any concave curvature in this interval the minimum value for $(1/k(x))/n_2^2$ is at least 0.5 mm$^{-1}$, preferably at least 0.6 mm$^{-1}$, more preferably at least 0.75 mm$^{-1}$, even more preferably at least 0.85 mm$^{-1}$ and most preferably at least 1.0 mm$^{-1}$, wherein $P_1$ defines the x-position at which the outer diameter of the glass syringe barrel is $0.95 \times d_2$ and $P_2$ is $P_1+3 \times n_2$.

In an embodiment 3 of the process 1 according to the invention, the process 1 is designed according to its embodiment 2, wherein shaping in process step III) is performed in such a way that in the interval between $x=P_1$ and $x=P_2$ the maximum value of the first derivative $f'(x)_{max}$ of f(x) is less than 18, even more preferably less than 15, even more preferably less than 10 and most preferably less than 5.

In an embodiment 4 of the process 1 according to the invention, the process 1 is designed according to anyone of its embodiments 1 to 3, wherein shaping in process step III) is performed in such a way that $r_2$ is in the range from 1.2 to 3.1 mm, preferably in the range from 1.4 to 2.9 mm, more preferably in the range from 1.6 to 2.7 mm, even more preferably in the range from 1.8 to 2.5 mm and most preferably in the range from 2.0 to 2.3 mm.

In an embodiment 5 of the process 1 according to the invention, the process 1 is designed according to anyone of its embodiments 1 to 4, wherein $d_2$ is in the range from 6 to 15 mm, preferably in the range from 6.5 to 14 mm, more preferably in the range from 7 to 13 mm, even more preferably in the range from 7.5 to 12 mm and most preferably in the range from 8 to 11 mm.

In an embodiment 6 of the process 1 according to the invention, the process 1 is designed according to anyone of its embodiments 1 to 5, wherein $n_2$ is in the range from 0.6 to 1.6 mm, preferably in the range from 0.7 to 1.5 mm, more preferably in the range from 0.8 to 1.4 mm, even more preferably in the range from 0.9 to 1.3 mm and most preferably in the range from 1 to 1.2 mm.

In an embodiment 7 of the process 1 according to the invention, the process 1 is designed according to anyone of its embodiments 1 to 6, wherein shaping in process step III) is performed in such a way that a constriction region is formed that is located between the cone region and the shoulder region, the constriction region having a first end that is adjacent to the second end of the cone region, a second end that is adjacent to the first end of shoulder region and an outer contour $c_3$, wherein the constriction region has a length $l_1'$, a minimum outer diameter $d_1' < d_1$ below the first end of the constriction region and an outer diameter $d_1''$ at the second end of the constriction region.

In an embodiment 8 of the process 1 according to the invention, the process 1 is designed according to its embodiment 7, wherein shaping in process step III) is performed in such a way that the outer contour $c_3$ of the glass syringe barrel in the constriction region is conically shaped with $d_1' < d_1''$ and wherein at the second end of the constriction region $c_3$ merges into $c_1$ without any offset.

In an embodiment 9 of the process 1 according to the invention, the process 1 is designed according to its embodiment 8, wherein shaping in process step III) is performed in such a way that in the constriction region a first line that runs parallel to the longitudinal axis $L_{barrel}$ and a second line that runs parallel to $c_3$ and that runs in the same plane as the first line include an angle γ, and wherein γ is in the range from 0.3 to 2.5°, preferably in the range from 0.5 to 2.0° and most preferably in the range from 0.7 to 1.5°.

In an embodiment 10 of the process 1 according to the invention, the process 1 is designed according to anyone of its embodiments 1 to 9, wherein shaping in process step III) is performed in such a way that $l_1$ or, in case of a constriction region, the total length $l_1+l_1'$, is in the range from 8 to 12 mm, preferably in the range from 8.75 to 10.5 mm, more preferably in the range from 8.5 to 10 mm, even more preferably in the range from 8.6 to 9.8 mm, even more preferably in the range from 8.7 to 9.6 and most preferably in the range from 9.4 to 9.6 mm.

In an embodiment 11 of the process 1 according to the invention, the process 1 is designed according to anyone of its embodiments 7 to 10, wherein shaping in process step III) is performed in such a way that $l_1'$ is in the range from 1 to 3 mm, preferably in the range from 1.1 to 2.5 mm, more preferably in the range from 1.2 to 2 mm, even more preferably in the range from 1.3 to 1.8 mm and most preferably in the range from 1.4 to 1.6 mm.

In an embodiment 12 of the process 1 according to the invention, the process 1 is designed according to anyone of its embodiments 1 to 11, wherein shaping in process step III) is performed in such a way that $d_1$ is in the range from 4 to 5 mm, preferably in the range from 4.1 to 4.8 mm, more preferably in the range from 4.2 to 4.6 mm, even more preferably in the range from 4.3 to 4.45 mm and most preferably in the range from 4.40 to 4.42 mm. Preferably, $d_1$ is the maximum outer diameter of the cone region. It is furthermore preferred that the second end of the cone region preferably corresponds to the point at which the outer diameter $d_1$ exceeds a value of 4.4 mm.

In an embodiment 13 of the process 1 according to the invention, the process 1 is designed according to anyone of its embodiments 7 to 12, wherein shaping in process step III) is performed in such a way that s $d_1'$ is in the range from 3.4 to 5.2 mm, preferably in the range from 3.6 to 5 mm, more preferably in the range from 3.8 to 4.8 mm, even more preferably in the range from 4 to 4.6 mm and most preferably in the range from 4.2 to 4.4 mm.

In an embodiment 14 of the process 1 according to the invention, the process 1 is designed according to anyone of its embodiments 7 to 13, wherein shaping in process step III) is performed in such a way that the maximum thickness of the glass in the constriction region is in the range from 1.3 to 2.1 mm, preferably in the range from 1.4 to 2 mm, more preferably in the range from 1.5 to 1.9 mm, even more preferably in the range from 1.6 to 1.8 mm and most preferably in the range from 1.65 to 1.75 mm.

In an embodiment 15 of the process 1 according to the invention, the process 1 is designed according to anyone of its embodiments 7 to 13, wherein shaping in process step III) is performed in such a way that the minimum thickness of the glass in the constriction region is in the range from 1.1 to 1.9 mm, preferably in the range from 1.2 to 1.8 mm, more preferably in the range from 1.3 to 1.7 mm, even more preferably in the range from 1.4 to 1.6 mm and most preferably in the range from 1.45 to 1.55 mm.

In an embodiment 16 of the process 1 according to the invention, the process 1 is designed according to anyone of its embodiments 1 to 15, wherein shaping in process step III) is performed in such a way that the shoulder region is characterized by an outer shoulder angle α in the range from 6 to 28°, preferably in the range from 8 to 22°, more preferably in the range from 9 to 16°, even more preferably in the range from 10 to 15° and most preferably in the range from 11 to 14°.

In an embodiment 17 of the process 1 according to the invention, the process 1 is designed according to anyone of its embodiments 1 to 16, wherein shaping in process step III) is performed in such a way that the shoulder region is characterized by an inner shoulder angle β in the range from 22 to 50° preferably in the range from 25 to 40°, more preferably in the range from 26 to 35°, even more preferably in the range from 27 to 32° and most preferably in the range from 28 to 31°.

In an embodiment 18 of the process 1 according to the invention, the process 1 is designed according to anyone of its embodiments 1 to 17, wherein shaping in process step III) is performed in such a way that, if $n_s$ is the glass thickness in the shoulder region, measured at the point of the inner shoulder surface at which the surface for the first time forms an angle of 30° with longitudinal axis $L_{barrel}$, $n_s$ is in the range from 1.2 to 2 mm, preferably in the range from 1.3 to 1.8 mm, more preferably in the range from 1.3 to 1.6 mm, even more preferably in the range from 1.35 to 1.5 mm and most preferably in the range from 1.35 to 1.45 mm.

In an embodiment 19 of the process 1 according to the invention, the process 1 is designed according to anyone of its embodiment 1 to 18, wherein the process further comprises the step of: roughening the outer surface of glass syringe barrel in the cone region or applying coating onto the outer surface of glass syringe barrel in the cone region.

In an embodiment 20 of the process 1 according to the invention, the process 1 is designed according to anyone of its embodiment 1 to 19, wherein the process further comprises the step of: cutting the glass tube, while rotating around its major axis, at a predetermined position above the first end to obtain a glass tube with a length $l_{tube}$ comprising a first end that has been shaped by means of process steps I) to III) and second end, wherein cutting can be accomplished mechanically by means of a cutting device or can be accomplished thermally by means of a flame with which the glass is molten at the predetermined position and is then pulled apart; heating the second end of the glass tube, while rotating around its major axis, to a temperature above its glass transition temperature, preferably above its softening temperature, with a heating element, preferably with a flame; while the glass tube is rotating around its major axis, shaping the second end that has been heated using one or more molding tools that act on predetermined positions of the outer surface of the glass tube at the first end to form a finger flange.

In an embodiment 21 of the process 1 according to the invention, the process 1 is designed according to anyone of its embodiment 1 to 20, wherein the glass is of a type selected from the group consisting of is selected from the group consisting of a borosilicate glass, an aluminosilicate glass and fused silica.

In an embodiment 22 of the process 1 according to the invention, the process 1 is designed according to anyone of its embodiment 1 to 21, wherein the process further comprises the step of superimposing at least a part of the interior surface of the body region with a coating.

A contribution to solving at least one of the objects according to the invention is made by an embodiment 1 of a glass syringe barrel 2 obtainable by the process of the invention according to any of its embodiments 1 to 22. In a preferred embodiment of the glass syringe barrel 2, this glass syringe barrel 2 shows the technical features of the glass syringe barrel 1 of the invention and the technical features of each glass syringe barrel contained in the plurality 1 or 2 of glass syringe barrels of the invention according to any of its embodiments, respectively.

A contribution to solving at least one of the objects according to the invention is made by an embodiment 1 of a syringe comprising a glass syringe barrel 1 according to any of its preferred embodiments, a plurality 1 or 2 of glass syringe barrels according to any of its preferred embodiments, or the glass syringe barrel 2 according to any of its preferred embodiments; a plunger stopper that has been pushed into the bottom end of the glass syringe barrel or into the bottom end of each of the glass syringe barrels contained in the plurality 1 or 2 of glass syringe barrels.

In an embodiment 2 of the syringe according to the invention, the syringe further comprises a pharmaceutical composition that is filled into at least a part of the inner volume of the body region.

Glass Syringe Barrel

The glass syringe barrel according to the invention may have any size or shape which the skilled person deems appropriate in the context of the invention. The first end of the glass syringe barrel an opening in the form of a channel located within the cone region through which a pharmaceutical composition that is contained in the glass syringe can be squeezed out of the glass syringe barrel and a second end (that is preferably provided with a finger flange) into which a plunger stopper can be pushed. Preferably, the glass syringe barrel is of a one-piece design that is prepared by providing a glass tube, preferably in form of a hollow cylinder, and forming the conically shaper upper portion, thereby obtaining the cone and the shoulder region (and optionally constriction region) and by forming a finger flange at the opposed end of the glass tube. A preferred glass syringe barrel is a prefilled glass syringe barrel that is filled with a pharmaceutical preparation. Preferably, the glass syringe barrel is rotationally symmetrical around the longitudinal axis $L_{barrel}$ that preferably goes perpendicular through the centre of the body region.

Glass

The glass of the glass syringe barrel be any type of glass and may consist of any material or combination of materials which the skilled person deems suitable in the context of the invention. Preferably, the glass is suitable for pharmaceutical packaging. Particularly preferable, the glass is of type I, more preferably type I b, in accordance with the definitions of glass types in section 3.2.1 of the European Pharmacopoeia, 7th edition from 2011. Additionally, or alternatively preferable to the preceding, the glass is selected from the group consisting of a borosilicate glass, an aluminosilicate glass, soda lime glass and fused silica; or a combination of at least two thereof. For the use in this document, an aluminosilicate glass is a glass which has a content of $Al_2O_3$ of more than 8 wt.-%, preferably more than 9 wt.-%, particularly preferable in a range from 9 to 20 wt.-%, in each case based on the total weight of the glass. A preferred aluminosilicate glass has a content of $B_2O_3$ of less than 8 wt.-%, preferably at maximum 7 wt.-%, particularly preferably in a range from 0 to 7 wt.-%, in each case based on the total weight of the glass. For the use in this document, a borosilicate glass is a glass which has a content of $B_2O_3$ of at least 1 wt.-%, preferably at least 2 wt.-%, more preferably at least 3 wt.-%, more preferably at least 4 wt.-%, even more preferably at least 5 wt.-%, particularly preferable in a range from 5 to 15 wt.-%, in each case based on the total weight of the glass. A preferred borosilicate glass has a content of $Al_2O_3$ of less than 7.5 wt.-%, preferably less than 6.5 wt.-%, particularly preferably in a range from 0 to 5.5 wt.-%, in each case based on the total weight of the glass. In a further aspect, the borosilicate glass has a content of $Al_2O_3$ in a range from 3 to 7.5 wt.-%, preferably in a range from 4 to 6 wt.-%, in each case based on the total weight of the glass.

A glass which is further preferred according to the invention is essentially free from B. Therein, the wording "essentially free from B" refers to glasses which are free from B which has been added to the glass composition by purpose. This means that B may still be present as an impurity, but preferably at a proportion of not more than 0.1 wt.-%, more preferably not more than 0.05 wt.-%, in each case based on the weight of the glass.

Shape of the Outer Contour in a Defined Area of the Luer Cone

An important element of the glass syringe barrel 1 according to the invention, of the glass syringe barrels contained in the plurality 1 of glass syringe barrels according to the invention and of the glass syringe barrel 2 according to the invention is the shape of the outer contour in the shoulder region that is formed in process step III) of the process 1 according to the present invention, particularly the outer contour in the concave and substantially circular arc-shaped area of the shoulder region. The outer contour in the shoulder region is characterized in that $r_1$, i. e. the radius of the concave and substantially circular arc-shaped area $c_1$ beginning below the second end of the cone region, is in the range from 0.4 to 3 mm. Furthermore, if the glass syringe barrel further comprises a constriction region that is localized between the cone region and the shoulder region and that is characterized by an outer contour $c_3$, it is also preferred that the glass syringe barrel in the constriction region is conically shaped in such a way that the diameter of the constriction region increases towards the shoulder region. In this context it is particularly preferred that the outer contour of the glass syringe barrel at the second end of the constriction region merges into the outer contour of the glass syringe barrel at the first end of the shoulder region without any offset.

Pharmaceutical Composition

In the context of the invention, every liquid pharmaceutical composition which the skilled person deems suitable to be used in a syringe comes into consideration. A pharmaceutical composition is a composition comprising at least one active ingredient. A preferred active ingredient is a vaccine. A further preferred pharmaceutical composition is a parenterialium, i.e. a composition which is intended to be administered via the parenteral route, which may be any route which is not enteral. Parenteral administration can be performed by injection, e.g. using a needle (usually a hypodermic needle) and a syringe.

Measurement Methods

The following measurement methods are to be used in the context of the invention. Unless otherwise specified, the measurements have to be carried out at an ambient temperature of 23° C., an ambient air pressure of 100 kPa (0.986 atm) and a relative atmospheric humidity of 50%.

Determination of the Local Curvature k(x)

The local curvature k(x) of the outer contour of the glass syringe barrel in the shoulder region defined by the function f(x) can be determined in a non-destructive manner using a profile projector. This approach is particularly suitable for glass syringe barrels that have been chemically and/or thermally tempered and that therefore cannot be easily sliced in half without the glass cracking or bursting. For determining the local curvature k(x) in a non-destructive manner the outer contour of the glass syringe barrels is visualized using a Mitutoyo PJ-3000 profile projector. The profile projector has a 10× magnification and is operated with transmitted light illumination. The barrels are placed in Hallbrite® BHB (a butyloctyl salicylate obtainable from the Hallstar Company, Chicago, USA), which is filled into a glass bowl. Hallbrite® BHB is used to visualize the outer contour of the barrel. It is ensured that the cross-section of the glass syringe barrel that is inspected in the profile projector corresponds to the plane that is centrically located in the glass syringe barrel and that comprises the longitudinal axis $L_{barrel}$ of the glass syringe barrel, i. e. the axis that goes perpendicular through the barrel (see FIGS. 6A and 6B).

To improve the measuring accuracy, the outer contour of the glass syringe barrel in the shoulder region can also be determined from a physical cross-sectional cut parallel along to the longitudinal axis $L_{barrel}$ of the barrel (it is again ensured that the cross-section of the glass syringe barrel corresponds to the plane that is centrically located in the glass syringe barrel and that comprises the longitudinal axis glass syringe barrel as shown in FIG. 4). For preparation without breakage, the barrel may be embedded into transparent 2-component epoxy resin, for example STRUERS GmbH, EpoFix Resin, or other suitable materials. After curing of the epoxy resin, a cross-sectional cut parallel along to the barrel axis can be achieved by machine-supported sawing, grinding and polishing. Geometrical features of the barrel can then be determined (measured) by means of non-distorting image capturing and geometrical analysis software tools.

The relevant outer contour of the outer surface of the glass syringe barrel in the shoulder region can be extracted and numerically approximated from the images obtained by means of the two approaches described above. For the extraction of the relevant contour of the outer surface, the images undergo the image processing steps implemented in Python [https://www.python.org/] based on the image processing library OpenCV [https://open-cv.org/].

First, the images are denoised using a median filter. The denoised images are then processed with an edge detection algorithm based on a Sobel filter, in which the contours are identified by thresholding the gradient image. For the calculation of slopes and curvatures, the extracted contours are numerically approximated by a univariate spline of order 5. The radii of curvature R(x) are then given by the formula $$R = \frac{\left\{1 + \left(\frac{dx}{dy}\right)^2\right\}^{\frac{3}{2}}}{\frac{d^2x}{dy^3}}$$

wherein R(x)=1/k(x).

Determination of $r_1$ and $r_2$

In the images obtained by means of the two approaches described above $r_1$ can be determined geometrically by applying a bevel circle to the first inflection point IP (i. e. the first one that appears when entering the outer contour of the shoulder region from the top of the glass syringe barrel) of function f(x) (i. e. the first point at which the condition f"(x)=0 is fulfilled) and to a straight line extending the outer contour of the cone region, as shown in FIG. 7. $r_2$ can also be determined geometrically by applying a circle adjacent to a straight line extending the outer contour of the body region and by increasing the diameter of the circle step by step until a maximum overlap between the outer contour of the shoulder region and a segment of the circle is reached (see again FIG. 7). The radius of the thus obtained circle is $r_2$.
Determination of $n_s$ In the images obtained by means of the two approaches described above the thickness of the glass in the shoulder region $n_s$ is measured at that point $P_3$ of shoulder region at which a tangent at the outer surface for the first time forms an angle of 30° to the syringe axis $L_{barrel}$ as this is shown in FIG. 8. $n_s$ is determined in a direction perpendicular to that line. For that purpose, a line is drawn perpendicular to that tangent in $P_3$. The point at which this perpendicular line crosses the inner surface is named $P_4$. A third line is drawn that runs parallel to tangent and that goes through $P_4$. $n_s$ corresponds to the distance between these two parallel lines.
Determination of A and B In the images obtained by means of the two approaches described above the inner shoulder angle β is measured at that point of the inner shoulder whose distance to the syringe axis $L_{barrel}$ is $[d_{c,inner}+d_{2,inner}]/4$ as this is shown in FIG. 9. $d_{c,inner}$ corresponds to the inner diameter of the channel at the top end of the syringe barrel and $d_{2,inner}$ corresponds to the inner diameter of the body region. α is determined using an offline camera. A line is drawn on the longest straight part between the two radii. The angle is then measured by applying a horizontal line.
Determination of the Cone Breaking Force The cone breaking force is determined according to ISO 11040-4: 2015 C.2, wherein the following parameters have been selected:

| Method | Measurement system | Load cell | Test speed | sampling rate | Distance from tip end | Closure |
|---|---|---|---|---|---|---|
| selected values | tensile and compression testing machine | ≤2 kN | 25m/min | ≥100 Hz | 2-3 mm | LLA only |

Example 1 and Comparative Example 1

A glass tube having an outer diameter $d_2$ of 10.85 mm and a wall thickness $n_2$ of 1.1 mm made of borosilicate glass is loaded into the head of a rotary machine. While rotating around its longitudinal axis $L_{tube}$ one end of the glass tube (i. e. at the end of which the Luer cone will be localized) is heated to its softening point with flames (see FIG. 11A). While the glass tube is rotating around its longitudinal axis the end that has been heated is shaped using molding tools that act on predetermined positions of the outer surface of the glass tube at the first end to form the cone region that also comprises a constriction region and the shoulder region. In a first step a first molding tool is pressed against the outer surface of the glass tube at the first end to initiate the formation of the constriction region (see FIG. 11B). The first end is then further heated (see FIG. 11D) and a set of second molding tools is then pressed against the preformed outer surface of the glass tube at the first end to obtain the final shape of the cone region, the constriction region and the shoulder region (see FIG. 11E). The shape of the further molding tools as well as the angle in which these tools are pressed against the molten cone region ensure that the minimum radius of curvature between points $P_1$ and $P_2$ is maintained in the desired range.

In a further process step the glass tube, while rotating around its longitudinal, is cut at a predetermined position above the first end to obtain a glass tube with a length $l_{tube}$ comprising a first end that is cone shaped and second end. The glass tube is then heated at the second end, while rotating around its longitudinal, to a temperature above its glass transition temperature with a flame. While the glass tube is still rotating around its longitudinal, the second end is then shaped for the formation of a flinger flange by pressing appropriate molding tools against the outer surface of the glass tube at the second end.

500 glass syringe barrels have been prepared in the rotary machine. The outer contour in the shoulder region of one of the glass syringe barrels corresponds to the outer contour of the shoulder region in glass syringe barrels known in the prior art (Comparative Example).

|  | Comparative Example 1 | Example 1 |
|---|---|---|
| $r_1$ [mm] | 0.4 | 1.5 |
| $r_2$ [mm] | 1.8 | 2.3 |
| $(1/k(x))/n_2^2$ [mm$^{-1}$] | 0.17 | 0.74 |
| f'(x)$_{max}$ | 19 | 4.45 |
| Tip resistance Mean [%] | 100 | 183 |
| Tip resistance Median [N] | 142 | 275 |
| Tip resistance Median [%] | 100 | 194 |
| 1% Quantile [N] | 48.3 | 116.5 |

Example 2 and Comparative Example 2

Two glass syringe barrels (glass syringe barrel A and B, which corresponds to the glass syringe barrel in Comparative Example 1) are compared, both of which consist of a glass tube with an outer diameter of 10.85 mm. The shape of glass syringe barrel A is defined such that for the outer contour of the shoulder region a value of 0.5 mm has been obtained for $r_1$, whereas glass syringe barrel B was again the one described in Comparative Example 1 of the present application ($r_1$=0.4 mm).

For glass syringe barrels A and B the maximum tensile stresses in the transition region between the shoulder region and the cone region are calculated that would result when a force of 100 N is applied onto the cone of the syringes as shown in FIG. 12. The following results have been obtained (see FIGS. 13A and 13B):

|  | Comparative Example 2 (glass syringe barrel B) | Example 2 (glass syringe barrel B) |
|---|---|---|
| $r_1$ [mm] | 0.4 mm | 0.5 mm |
| maximum tensile stress [MPa] | 214 | 206 |

These results also show that by ensuring that the value for $r_1$ is in the particularly preferred range from 0.5 to 3 mm leads to an increased resistance towards pressures that are applied onto the cone region of the glass syringe barrel.

BRIEF DESCRIPTION OF THE DRAWINGS

Unless otherwise specified in the description or the particular figure.

DETAILED DESCRIPTION

Figure 1:
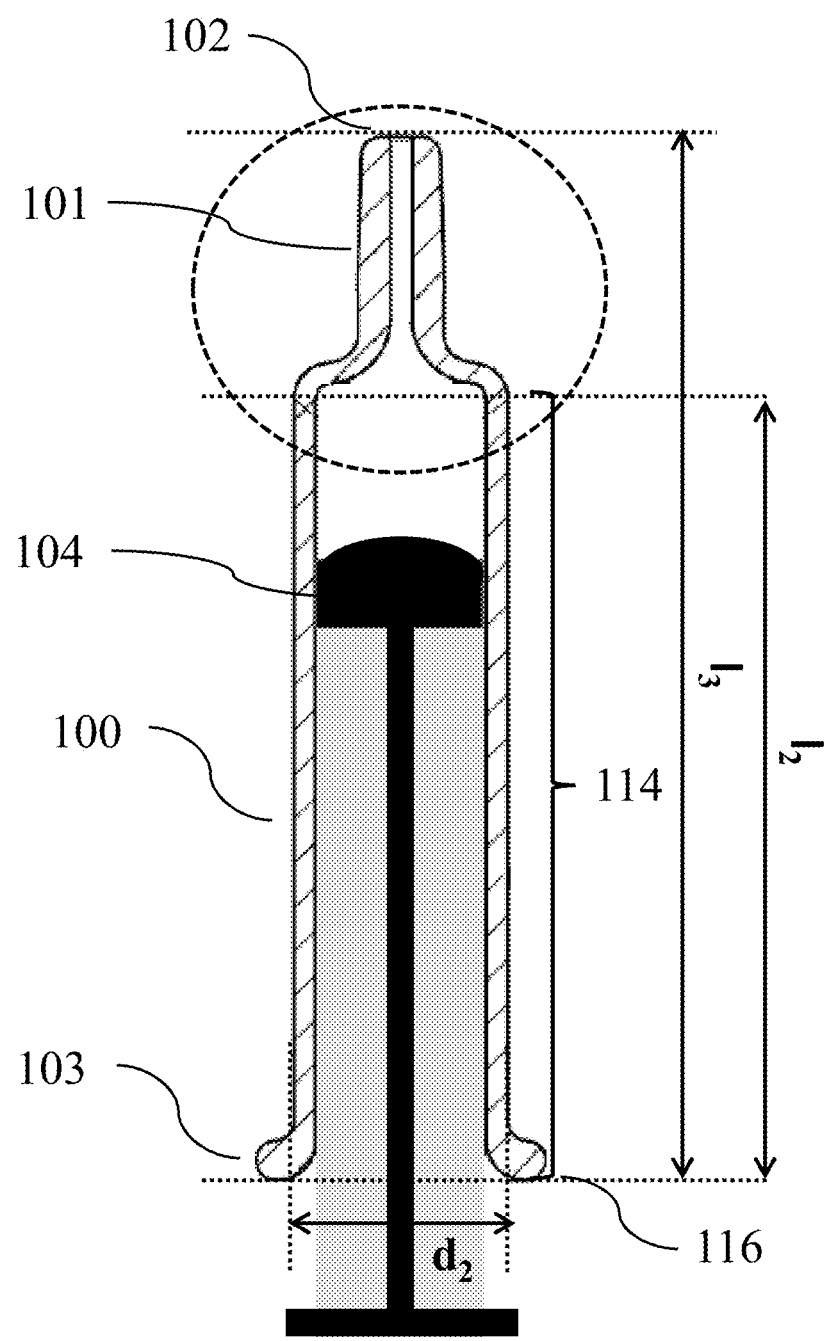
FIG. 1 shows a cross-sectional view of a syringe comprising a glass syringe barrel 100 according to the present invention into view a plunger stopper 104 has been introduced.

FIG. 1 shows a cross-sectional view of a syringe comprising a glass syringe barrel 100 according to the present invention having the length $l_3$ and an outer diameter $d_2$ in the body region 114 into view a plunger stopper 104 has been introduced. As can be seen in FIG. 1, the syringe barrel 100 comprises a top end 102 with a conically shaper upper portion 102 and a bottom end 103 into which the plunger stopper 104 has been introduced.

Figure 2:
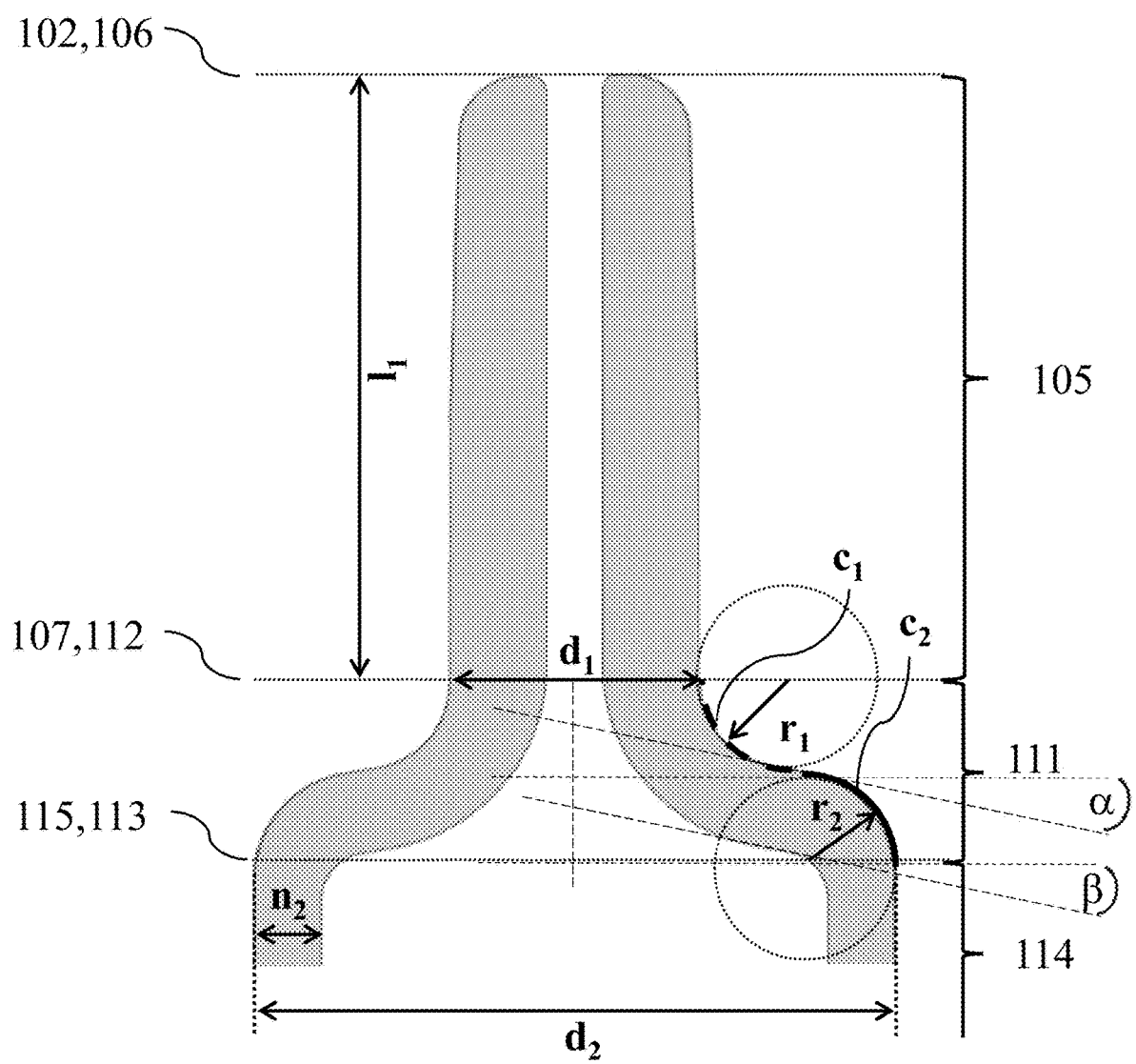
FIG. 2 shows a cross-sectional enlarged view of the top end of a glass syringe barrel 100 according to the present invention that comprises a conically shaped upper portion 101 in the form of a Luer cone.

FIG. 2 shows a cross-sectional enlarged view of the top end 102 of the glass syringe barrel 100 shown in FIG. 1 that comprises the conically shaped upper portion 101 (the section of the glass syringe barrel 100 that is shown in FIG. 2 corresponds to the area that is encompassed by the dotted circle in FIG. 1). As can be seen in FIG. 2, the conically shaped upper portion 101 of the glass syringe barrel 100 is in the form of a Luer-slip style connector and comprises in the embodiment shown in FIG. 2 a cone region 105 having a first end 106 that corresponds to the top end 102 of the glass syringe barrel 100 and a second end 107, wherein the cone region 105 has a length $l_1$ and an outer diameter $d_1$ at the second end 107. Adjacent to the cone region 105 is a shoulder region 111 having a first end 112 that is adjacent to the second end 107 of the cone region 105 and a second end 113, wherein the outer contour of the shoulder region 111 comprises a concave and substantially circular arc-shaped area $c_2$ (see the dashed and bold marked line in the upper part of the right side of the shoulder region) with an outer radius $r_1$ beginning below the second end 110 of the constriction region 108 and a convex and substantially circular arc-shaped area $c_3$ (see the continuous and bold marked line in the upper part of the right side of the shoulder region) with an outer radius $r_2$ beginning above the second end 113. As also shown in FIG. 2 the shoulder region 111 is characterized by an outer shoulder angle α and an inner shoulder angle β. Adjacent to the should region 111 is a body region 114 (see also FIG. 1) into which the syringe plunger 104 can be pushed, having a first end 115 that is adjacent to the second end 113 of the shoulder region 111 and a second end 116 that corresponds to the bottom end 103 of the glass syringe barrel 100, wherein the thickness of the glass in the body region 114 is $n_2$. The diameter $d_2$ of the body region 114 corresponds to the diameter of the glass tube 126 that is used to manufacture the glass syringe barrel 100 according to the present invention (see FIGS. 11A-11F).

Figure 3:
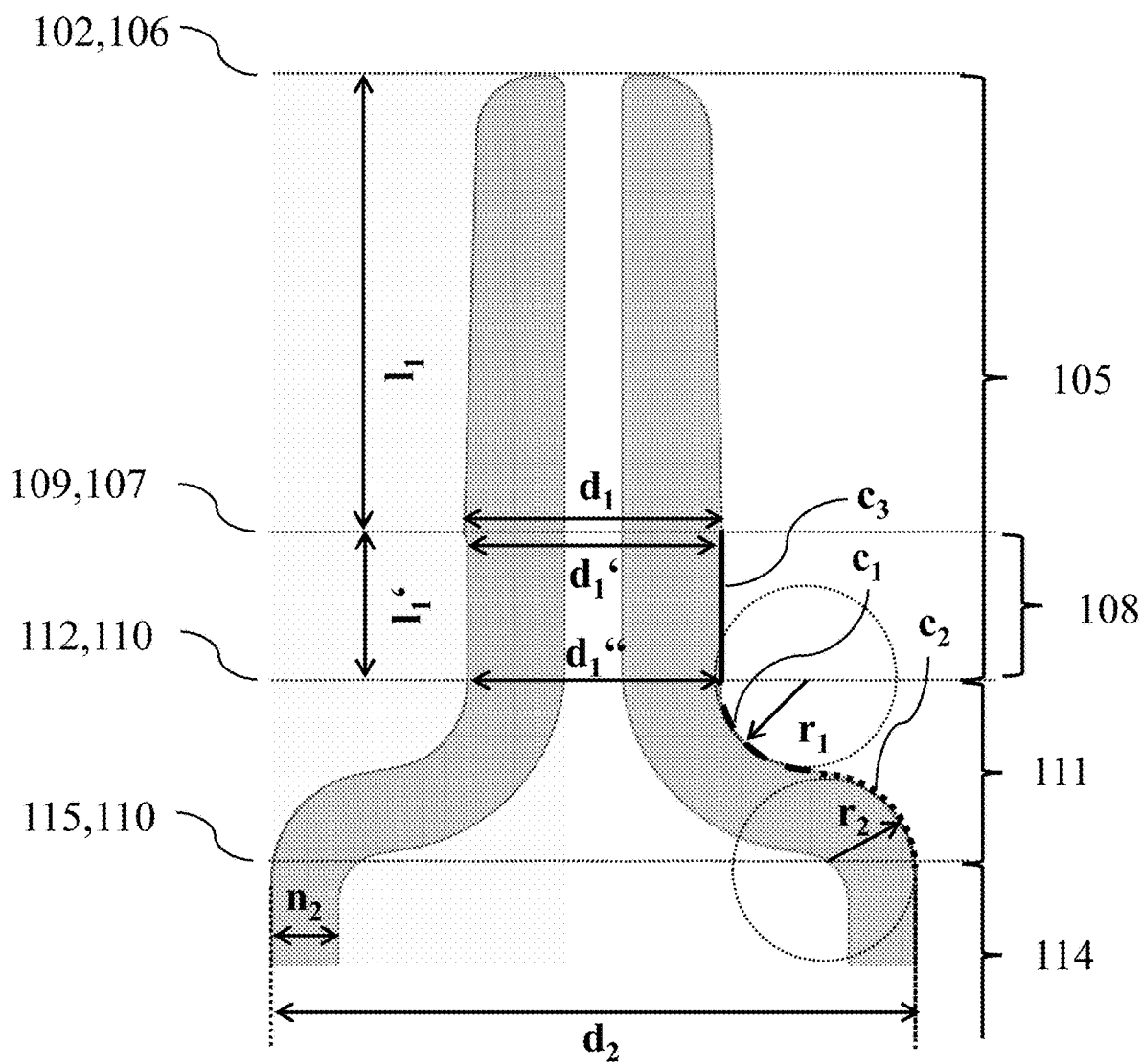
FIG. 3 shows a cross-sectional enlarged view of the top end 102 of a further glass syringe barrel 100 according to the present invention that comprises a conically shaped upper portion 101 in the form of a Luer cone, wherein the glass syringe barrel further comprises a constriction region 108 that is located between the cone region 105 and the should region 111.
Figure 4:
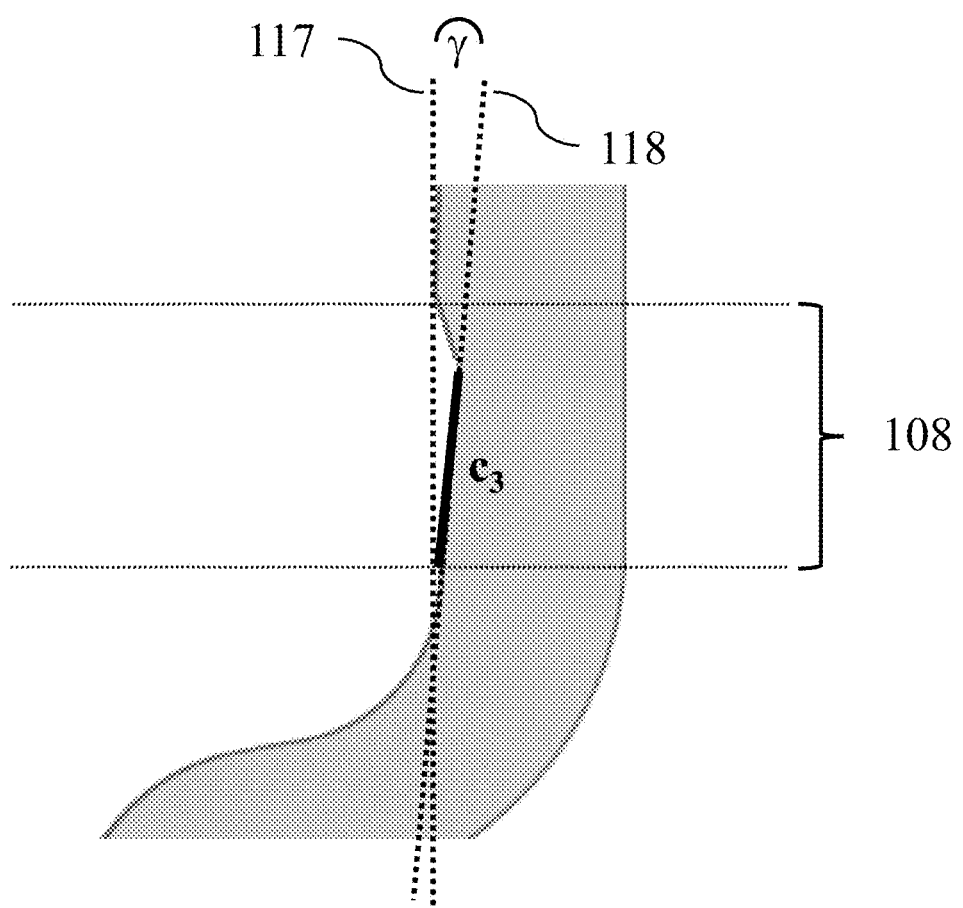
FIG. 4 shows the determination of angle γ in the constriction region 108.

FIG. 3 shows a cross-sectional enlarged view of the top end 102 of a further glass syringe barrel 100 according to the present invention that comprises a conically shaped upper portion 101 in the form of a Luer cone, wherein the glass syringe barrel further comprises a constriction region 108 that is located between the cone region 105 and the should region 111. The constriction region 108 comprises a first end 109 that is adjacent to the second end 107 of the cone region 105, a second end 110 that is adjacent to the first end 112 of shoulder region 111 and an outer contour $c_3$, wherein the constriction region 108 has a length $l_1'$, a minimum outer diameter $d_1' < d_1$ below the first end 109 of the constriction region 108 and an outer diameter $d_1''$ at the second end 110 of the constriction region 108. In this context it is furthermore preferred that the outer contour $c_3$ of the glass syringe barrel in the constriction region is conically shaped with $d_1' < d_1''$ and wherein at the second end of the constriction region $c_3$ merges into $c_1$ without any offset. It is also preferred that in the constriction region 108 a first line 117 that runs parallel to the longitudinal axis $L_{barrel}$ and a second line 118 that runs parallel to $c_3$ and that runs in the same plane as the first line 117 include an angle γ, wherein γ is in the range from 1 to 3°. FIG. 4 shows how to determine the angle γ in the constriction region 108, this angle defining the extend of the conical shape of the constriction region.

Figure 5A:
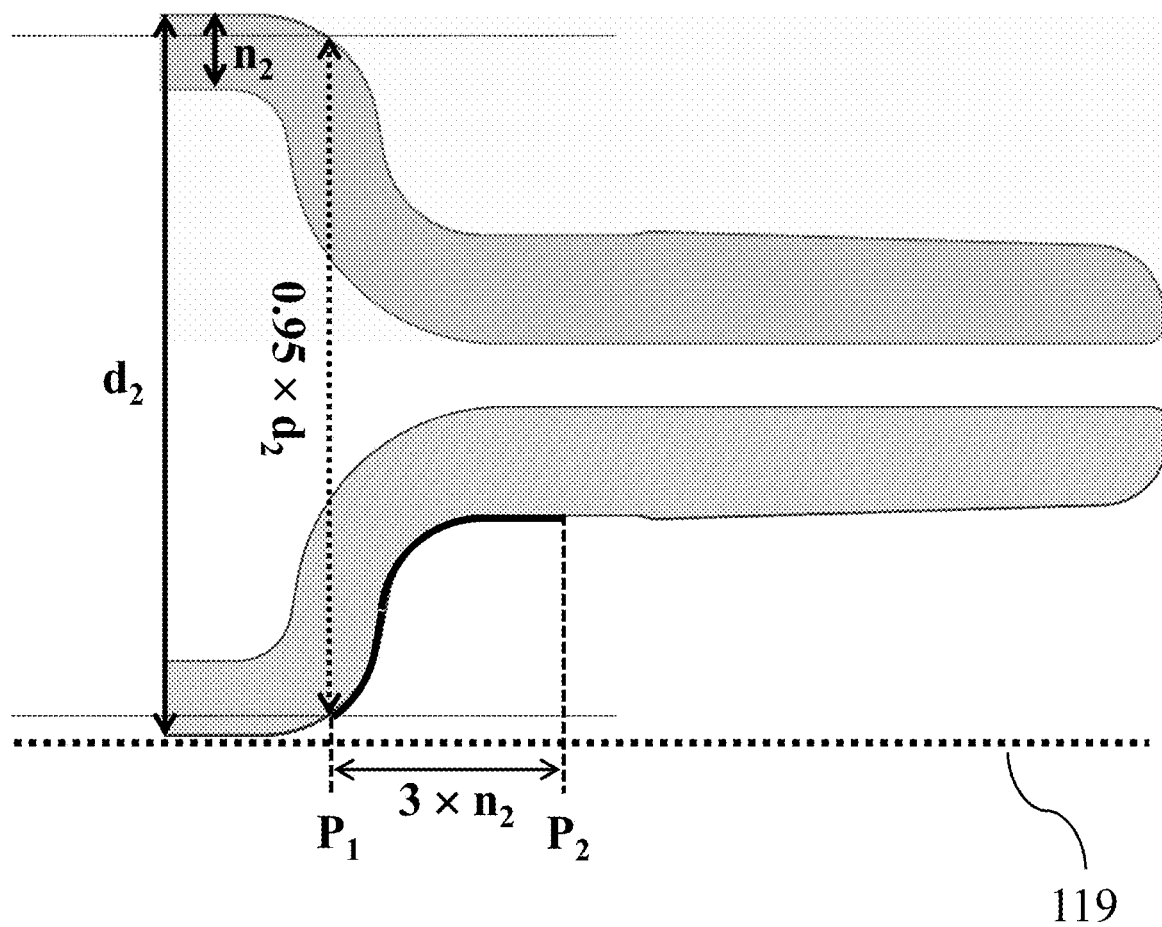
FIG. 5A shows a cross-sectional enlarged view of the top end 102 of the glass syringe barrel 100 shown in FIG. 3, wherein in contrast to FIG. 3 the glass syringe barrel 100 with the outer surface of the body region 114 is laying on a substrate 119.

The glass syringe barrel 100 according to the present invention is characterized by a well-defined outer contour in the transition region between the shoulder region 111 and, if present, of the constriction region 108 as well. If the glass syringe barrel 100 is placed on a plane horizontal substrate 119 with the outer surface of the body region 114 on it as shown in FIG. 5A, function f(x) defines the vertical distance between the substrate 119 and the outer surface of the glass syringe barrel 100 at a given position x and thus the outer contour of the glass syringe barrel 100 in that area (see FIG. 5B). From that function the curvature k(x) at a given position x of the outer contour can be calculated as $$k(x) = |f''(x)|/[1+f'(x)^2]^{3/2}).$$

The glass syringe barrel according to the present invention is now characterized in that interval between $x = P_1$ and x=$P_2$ for any concave curvature in this interval the minimum value for $(1/k(x))/n_2^2$ is at least 0.5 mm$^{-1}$, wherein $P_1$ defines the x-position at which the outer diameter of the glass syringe barrel 100 is 0.95×$d_2$ and $P_2$ is $P_1$+3×$n_2$ (see FIG. 5A).

Figure 5B:
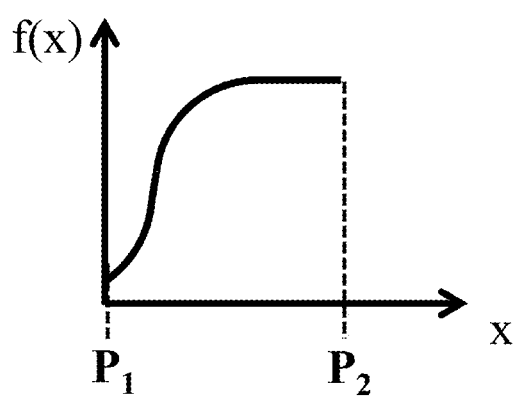
FIG. 5B shows function f(x) by means of which the curvature k(x) of the outer contour of the glass syringe barrel in the shoulder region 111 can be determined.
Figure 6A:
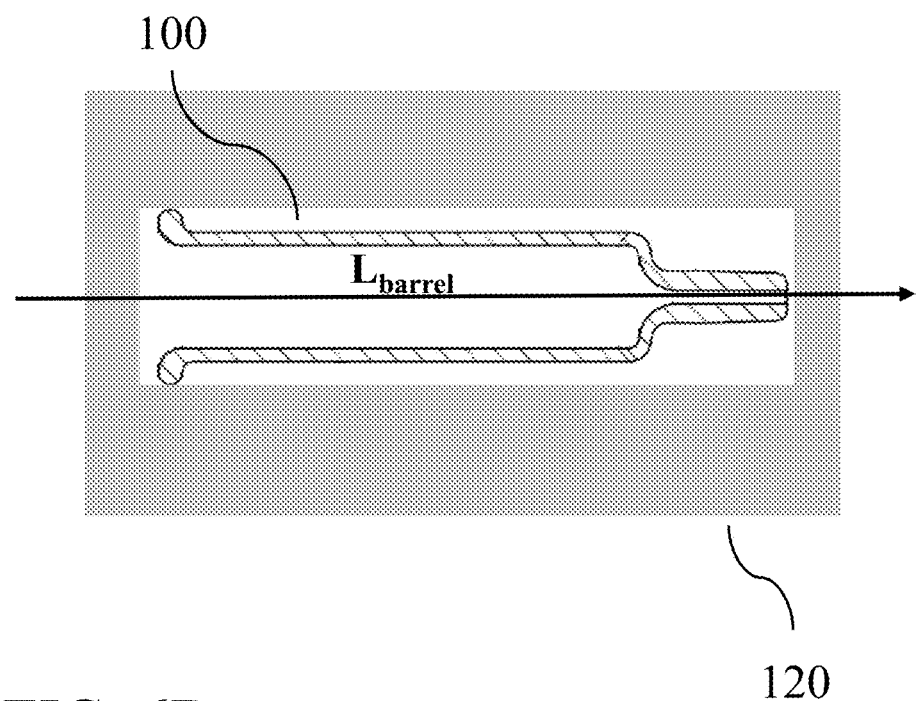
FIG. 6A shows in a side view the localization of plane 120 that is used to determine the local curvature of function f(x) within the range from $P_1$ to $P_2$.
Figure 6B:
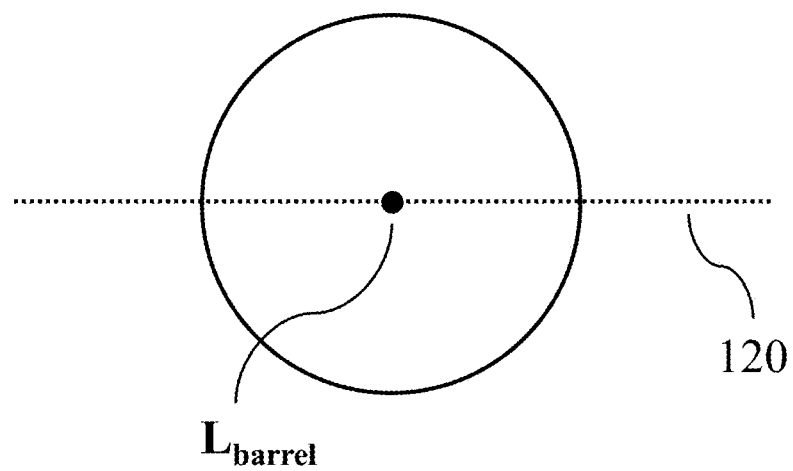
FIG. 6B shows in a top view the localization of plane 120 that is used to determine the local curvature of function f(x) within the range from $P_1$ to $P_2$.

FIGS. 6A and 6B show in a side view and in a top view the localization of plane 120 in the glass syringe barrel 100 that is used to determine the local curvature of function f(x) within the range from $P_1$ to $P_2$ by means of the approach that is shown in FIGS. 5A and 5B. Plane 120 corresponds to the plane that is centrically located in the glass syringe barrel 100 and that comprises the longitudinal axis $L_{barrel}$ of the glass syringe barrel 100.

Figure 7:
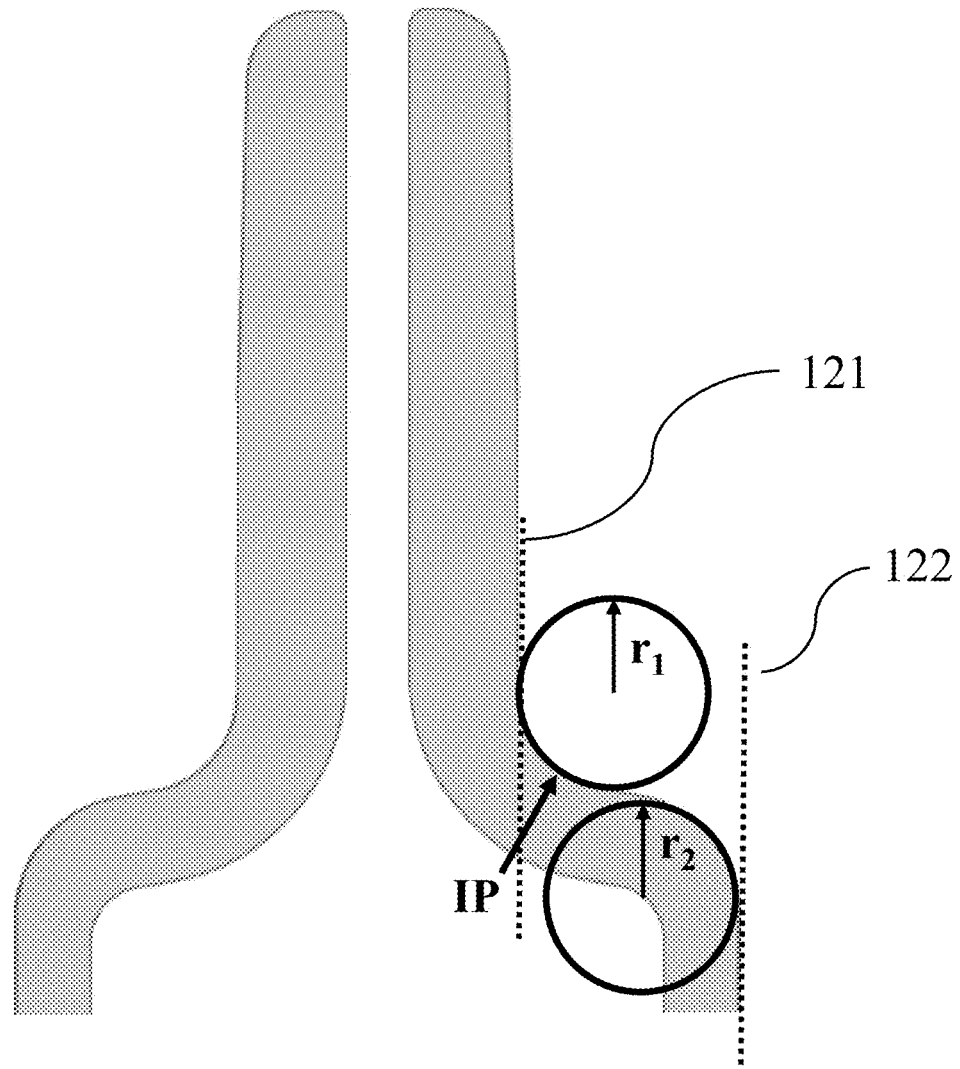
FIG. 7 shows the determination of $r_1$.

FIG. 7 shows how to determine the outer radius $r_1$ of the concave and substantially circular arc-shaped area $c_1$ of the shoulder region 111. $r_1$ can be determined geometrically in cross-sectional images of the glass syringe barrel 100 by applying a bevel circle to the first inflection point IP (i. e. the first one that appears when entering the outer contour of the shoulder region 111 from the top end 102 of the glass syringe barrel 100) of function f(x) (i. e. the first point at which the condition f"(x)=0 is fulfilled) and to a straight line 121 extending the outer contour of the cone region 105. $r_2$ can be determined geometrically by applying a circle adjacent to a straight line 122 extending the outer contour of the body region 114 and by increasing the diameter of the circle until a maximum overlap between the outer contour of the shoulder region 111 and a segment of the arc is reached. The radius of the thus obtained circle is $r_2$.

Figure 8:
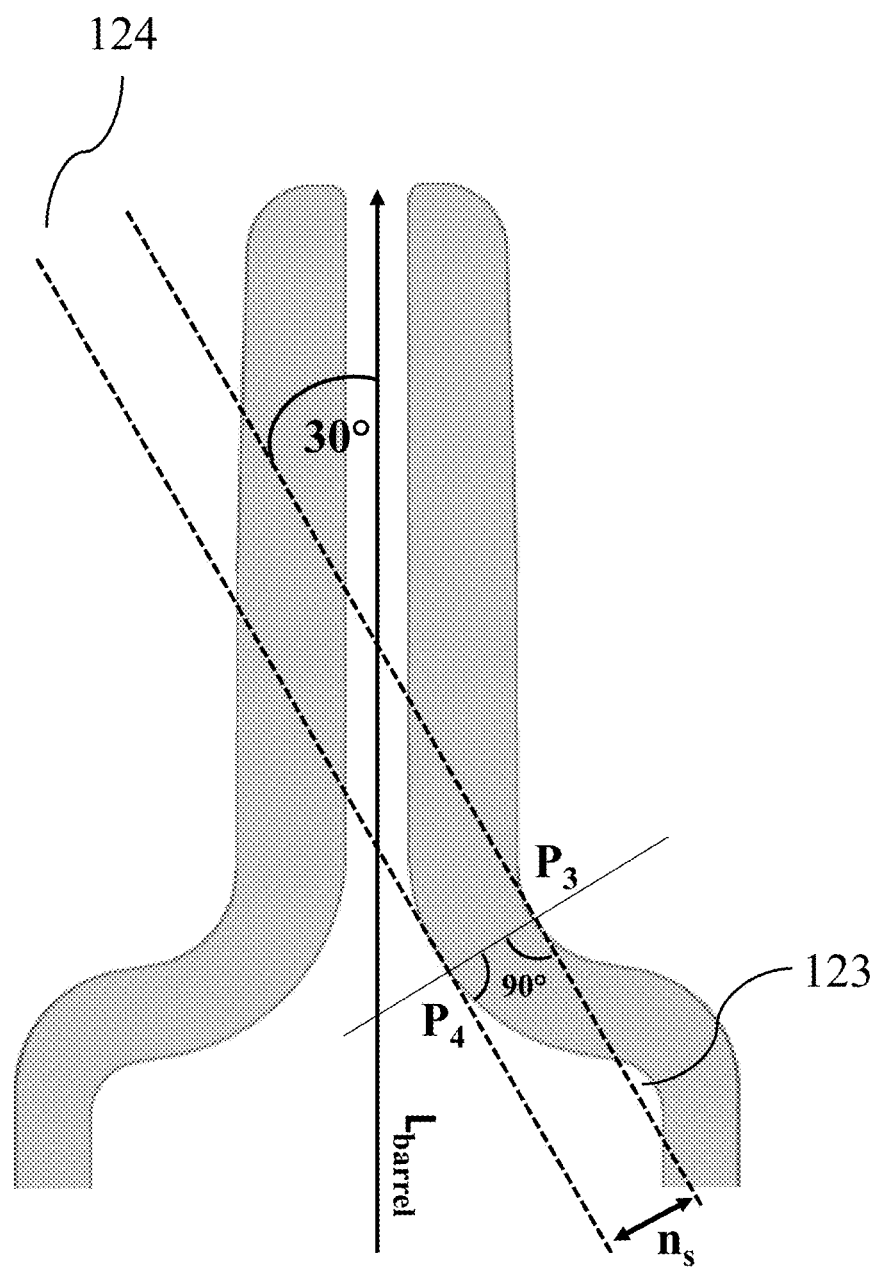
FIG. 8 shows the determination of $n_s$.

FIG. 8 shows how to determine the thickness $n_s$ of the glass in the shoulder region 111. $n_s$ is measured at that point $P_3$ of shoulder region at which a tangent at the outer surface for the first time forms an angle of 30° to the syringe axis $L_{barrel}$ as this is shown in FIG. 8. $n_s$ is determined in a direction perpendicular to that line. For that purpose, a line is drawn perpendicular to that tangent in $P_3$. The point at which this perpendicular line crosses the inner surface is named $P_4$. A third line is drawn that runs parallel to tangent and that goes through $P_4$. $n_s$ corresponds to the distance between these two parallel lines.

Figure 9:
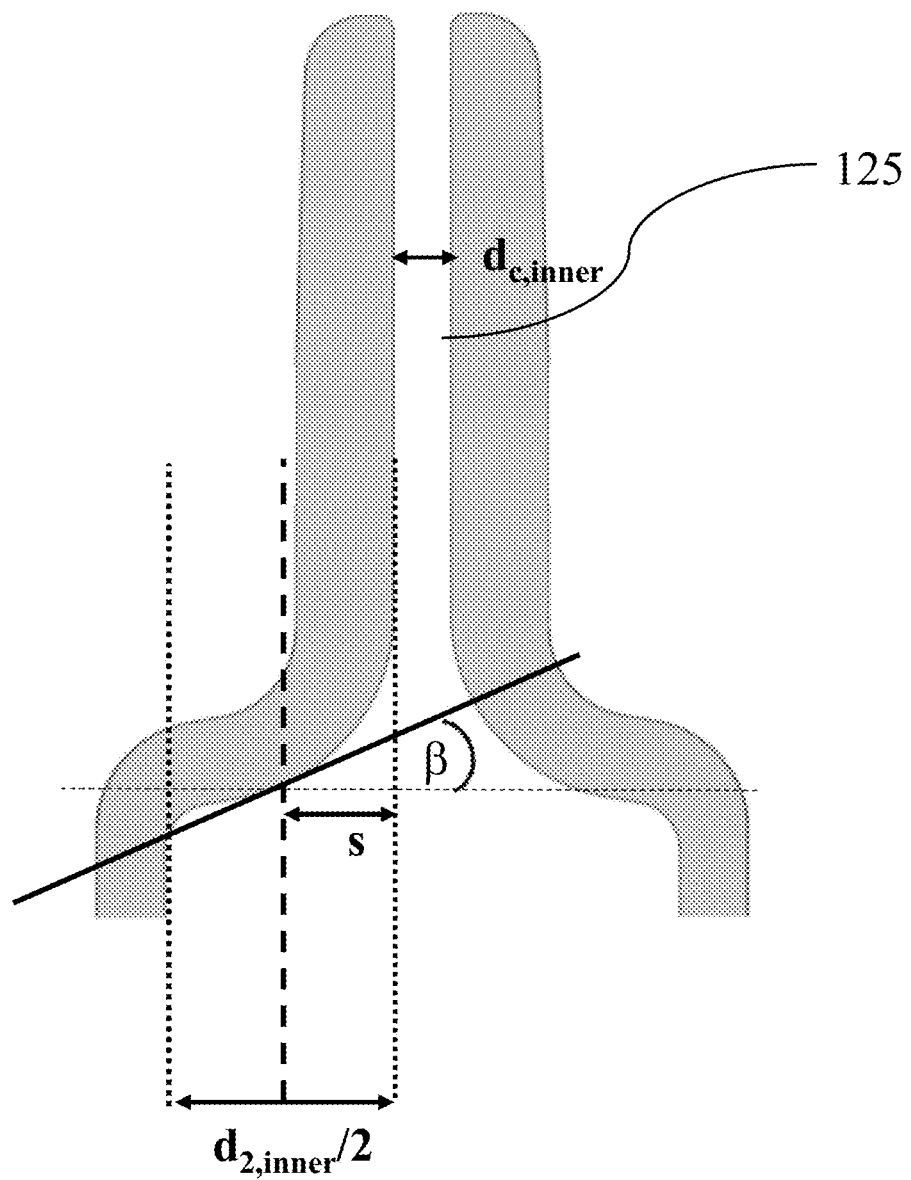
FIG. 9 shows the determination of β.

FIG. 9 shows how to determine the inner shoulder angle β. β is measured at that point of the inner shoulder whose distance to the syringe axis $L_{barrel}$ is $[d_{c,inner}+d_{2,inner}]/4$. $d_{c,inner}$ corresponds to the inner diameter of the channel 125 at the top end 102 of the glass syringe barrel 100 and $d_{2,inner}$ corresponds to the inner diameter of the body region 114.

Figure 10:
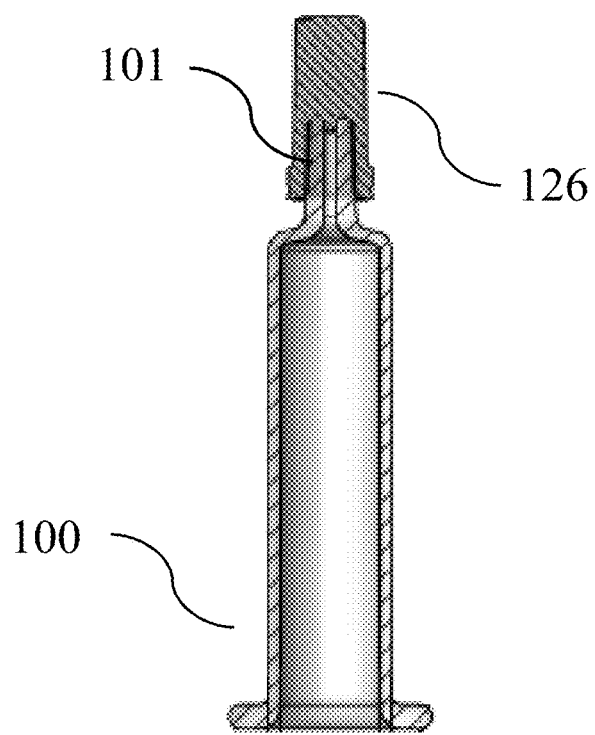
FIG. 10 shows a glass syringe barrel 100 according to the present invention with a tip cap 117 attached to the conically shaped upper portion 101.

FIG. 10 shows a glass syringe barrel 100 according to the present invention with a tip cap 126 attached to the conically shaped upper portion 101.

Figure 11A:
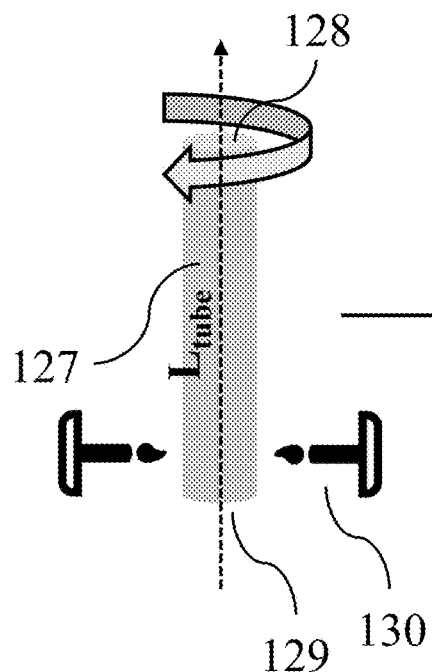
FIGS. 11A-F illustrate steps I), II) and III) of process 1 according to the invention for the preparation of a glass syringe barrel 100.
Figure 11B:
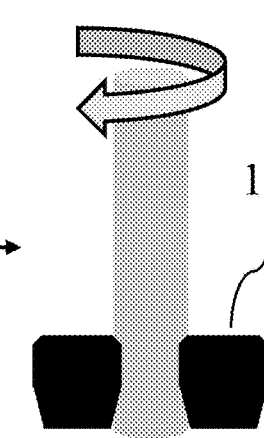
Figure 11C:
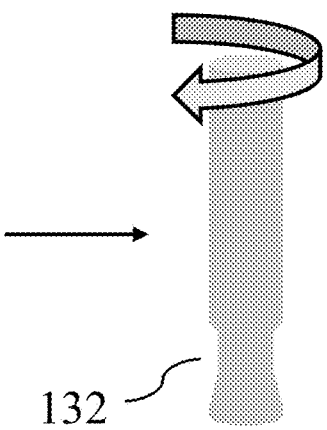
Figure 11D:
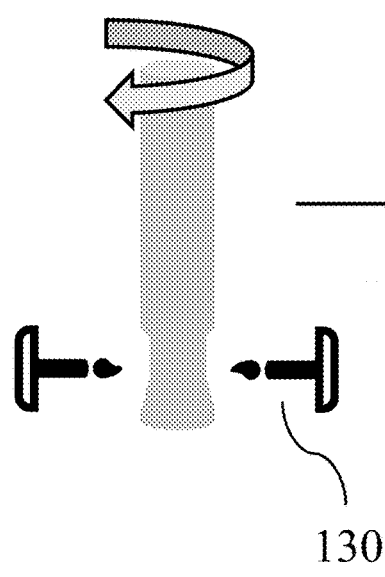
Figure 11E:
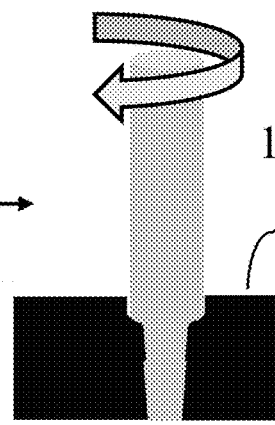
Figure 11F:
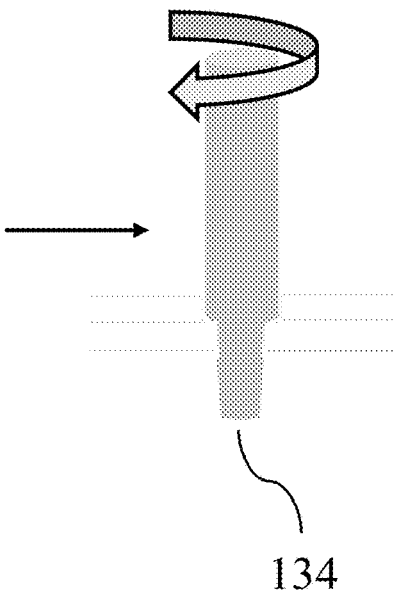
Figure 12:
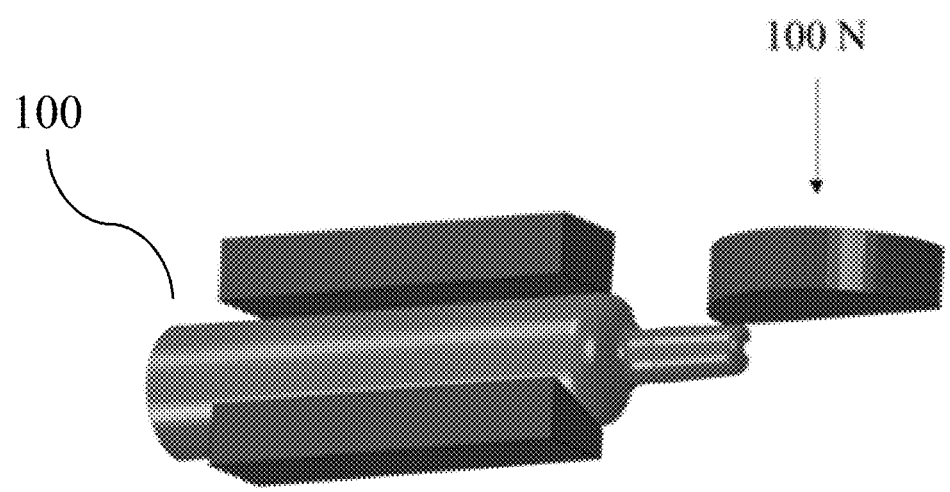
FIG. 12 illustrates the mechanical load that is applied onto the cone of the glass syringe barrels when calculating the maximum tensile stresses in Comparative Example 2 and Example 2.
Figure 13A:
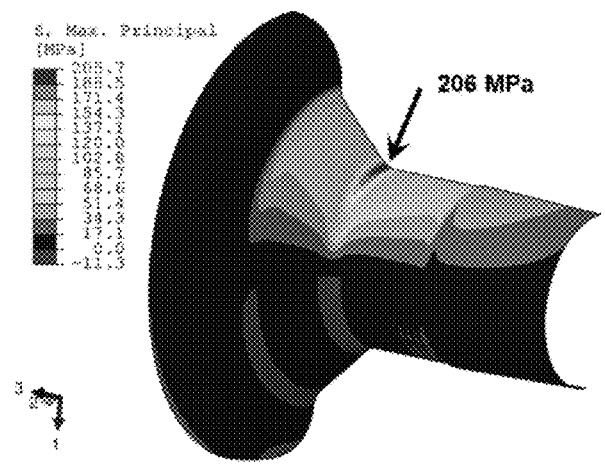
FIGS. 13A-B illustrate the results of the calculations in Comparative Example 2 and Example 2.
Figure 13B:
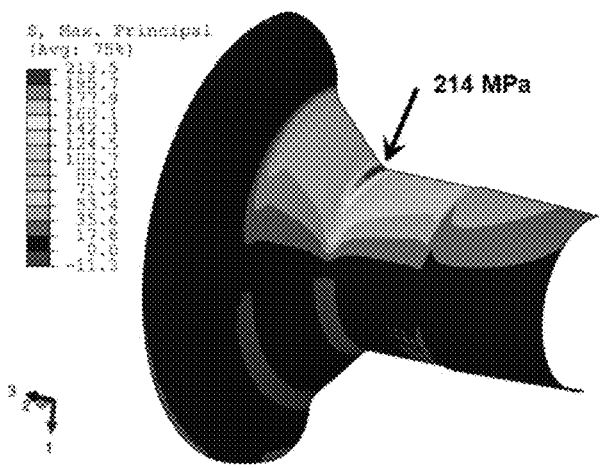

FIGS. 11A-F illustrate steps I), II) and III) of process 1 according to the invention for the preparation of a glass syringe barrel 100 according to the present invention. In process step I) a glass tube 127 having a longitudinal axis $L_{tube}$, a first end 129 and a further end 128 is loaded into a machine, preferably a rotary machine, the glass tube 127 having a wall thickness $n_2$ and an outer diameter $d_2$. In process step II) the glass tube 127, while rotating around its longitudinal axis, is heated to a temperature above its glass transition temperature, preferably above its softening temperature, with a heating element 130 (indicated by the candle flames shown on the left in FIG. 11A), preferably with a flame 130. In process step III), while the glass tube 127 is still rotating around its longitudinal axis, the first end 129 that has been heated is shaped by using molding tools 131 that act on predetermined positions of the outer surface of the glass tube 127 at the first end 129 to form a conically shaped upper portion 101 as shown in FIGS. 11B and 11E.

In the process shown in FIGS. 11A-11F the conically shaped upper portion 101 is formed in two steps: in a first step using a first set of molding tools 131 a Luer end precursor 132 is formed that does not have the final shape of the conically shaped upper portion 101 according to the present invention (see FIGS. 11B and 11C). The Luer cone precursor 132 is then again heated as shown in FIG. 11D and is then finally shaped using a second set of molding tools 133 as shown in FIG. 11E to obtain a glass tube 127 with finished conically shaped upper portion 101 (see FIG. 11E). The shape of the molding tools 131,133 that are used in this shaping process as well as the extent to which they are pressed against the molten region of the glass tube 127 have to be adopted to ensure that the desired geometry particularly in the transition state between the shoulder region 111 and the cone region 105 (or, if present, the constriction region 108) is obtained.

In a further process step V) the glass tube with finished conically shaped upper portion 101, while rotating around its longitudinal axis, is cut at a predetermined position above the first end 129 to obtain a glass tube with a length $l_{tube}$ comprising a first end 128 that has been shaped by means of process steps I) to III) and second end. In a further process step VI) the second end of the glass tube, while rotating around its longitudinal axis, is heated to a temperature above its glass transition temperature, preferably above its softening temperature, with a heating element, preferably with a flame. In a further process step VII), while the glass tube is rotating around its longitudinal axis, the second end that has been heated using is shaped using one or more molding tools that act on predetermined positions of the outer surface of the glass tube at the first end to, for example, form a finger flange (process steps V) to VII) are not shown in FIGS. 11A-11F).

LIST OF REFERENCE NUMERALS 100 glass syringe barrel according to the invention
101 conically shaped upper portion
102 top end
103 bottom end
104 plunger stopper
105 cone region
106 first end of the cone region 105 (=top end 102)
107 second end of the cone region 105 (=first end 112 of the shoulder region 111 or first end 109 of the constriction region 108)
111 shoulder region
112 first end of the shoulder region 111 (=second end 107 of the cone region 105 or second end 110 of the constriction region 108)
113 second end of the shoulder region 111 (=first end 115 of the body region 114)
114 body region
115 first end of the body region 114 (=second end 113 of the shoulder region 111)
116 second end of the body region 114 (=bottom end 103)
108 constriction region
109 first end of the constriction region 108 (=the second end 107 of the cone region 105)
110 second end of the constriction region 108 (=first end 112 of the should region 111)
117 first line
118 second line
119 plane and horizontal substrate
120 cross-sectional plane in the middle of the glass syringe barrel 100
121 elongation of the outer contour of the cone region 105

122 elongation of the outer contour of the body region 114
123 tangent at the outer surface of the shoulder region 111 that includes an angle of 30° with $l_{barrel}$
124 tangent at the inner surface of the shoulder region 111 that includes an angle of 30° with $l_{barrel}$
125 channel at the top end 102
126 tip cap
127 glass tube
128 further end of the glass tube
129 first end of the glass tube
130 heating element
131 first set of forming tools
132 Luer end precursor
133 second set of molding tools
134 glass tube with finished Luer end

What is claimed is:

1. A glass syringe barrel, comprising:
   a top end through which a liquid can be ejected;
   a bottom end into which a plunger stopper can be pushed;
   a longitudinal axis $L_{barrel}$ through the top and bottom ends; and
   a cone region having a first end that corresponds to the top end and a second end, the cone region has a length $l_1$ and has an outer diameter $d_1$ at the second end;
   a shoulder region having a first end that is adjacent to the second end of the cone region and a second end, wherein the shoulder region has an outer contour that comprises a concave and substantially circular arc-shaped area $c_1$ with an outer radius $r_1$ beginning below the second end of the cone region and a convex and substantially circular arc-shaped area $c_2$ with an outer radius $r_2$ beginning above the second end of the shoulder region;
   a body region having a first end that is adjacent to the second end of the shoulder region and a second end that corresponds to the bottom end, wherein the body region has an outer diameter $d_2$ and a glass thickness $n_2$, wherein $r_1$ is in a range from 0.5 to 3 mm; and
   a Luer cone breaking resistance that is at least 50 N for a 1% quantile and/or at least 145 N for a 50% quantile, wherein the outer radius $r_2$ is in a range from 1.4 to 2.9 mm.

2. The glass syringe barrel of claim 1, wherein the Luer cone breaking resistance is at least 80 N for the 1% quantile and/or at least 205 N for the 50% quantile.

3. The glass syringe barrel of claim 1, wherein the Luer cone breaking resistance is at least 110 N for the 1% quantile and/or at least 270 N for the 50% quantile.

4. The glass syringe barrel of claim 1, wherein the outer radius $r_1$ is in a range from 0.6 to 2.5 mm.

5. The glass syringe barrel of claim 1, wherein, if an outer surface of the body region is placed on a plane horizontal substrate, within any given cross-section of the glass syringe barrel that is located in a plane centrically located in the glass syringe barrel and comprising the longitudinal axis $L_{barrel}$ of the glass syringe barrel, a first function f(x) defines a vertical distance between the substrate and the outer surface at a given position x, $k(x)=|f''(x)/[1+f'(x)^2]^{3/2}|$ defines an absolute value of the curvature of f(x) at a given position x, and in an interval between $x=P_1$ and $x=P_2$ for any concave curvature in the interval a minimum value for $(1/k(x))/n_2^2$ is at least 0.5 mm$^{-1}$, wherein $P_1$ defines the x-position at which the outer diameter of the glass syringe barrel (100) is $0.95 \times d_2$ and $P_2$ is $P_1+3\times n_2$.

6. The glass syringe barrel of claim 5, wherein in the interval between $x=P_1$ and $x=P_2$ the maximum value of the first derivative f'(x) max of f(x) is less than 18.

7. The glass syringe barrel of claim 1, further comprising a constriction region that is located between the cone region and the shoulder region, the constriction region having a first end that is adjacent to the second end of the cone region, a second end that is adjacent to the first end of shoulder region and an outer contour $c_3$, wherein the constriction region has a length $l_1'$, a minimum outer diameter $d_1'<d_1$ below the first end of the constriction region and an outer diameter $d_1''$ at the second end of the constriction region.

8. The glass syringe barrel of claim 7, wherein the outer contour $c_3$ in the constriction region is conically shaped with $d_1'<d_1''$ and wherein at the second end of the constriction region, the outer contour $c_3$ in the constriction region merges into area $c_1$ without any offset.

9. The glass syringe barrel of claim 8, wherein in the constriction region a first line that runs parallel to the longitudinal axis $L_{barrel}$ and a second line that runs parallel to the outer contour $c_3$ and that runs in the same plane as the first line include an angle γ, wherein γ is in the range from 0.3 to 2.5°.

10. The glass syringe barrel of claim 7, wherein the maximum thickness of the glass in the constriction region is in the range from 1.3 to 2.1 mm.

11. The glass syringe barrel of claim 7, wherein the minimum thickness of the glass in the constriction region is in the range from 1.1 to 1.9 mm.

12. The glass syringe barrel of claim 1, wherein the shoulder region comprises an outer shoulder angle α in a range from 6 to 28°.

13. The glass syringe barrel of claim 1, wherein the shoulder region comprises an inner shoulder angle β in a range from 22 to 50°.

14. The glass syringe barrel of claim 1, wherein $n_s$ is the glass thickness in the shoulder region, measured at the point of the inner shoulder surface at which the surface for the first time forms an angle of 30° with longitudinal axis $L_{barrel}$, and wherein $n_s$ is in the range from 1.2 to 2 mm.

15. The glass syringe barrel of claim 1, wherein the barrel has a nominal volume V in a range from 0.5 to 11 ml.

16. The glass syringe barrel of claim 1, further comprising a coating that at least partially superimposes the interior surface of the body region.

17. The glass syringe barrel of claim 1, further comprising a needle attached to the cone region via a Luer connector and wherein the needle is sealed with a needle cap.

18. A syringe, comprising:
   the glass syringe barrel of claim 1; and
   a plunger stopper in the bottom end.

19. The syringe of claim 18, further comprising a pharmaceutical composition in an inner volume of the glass syringe barrel.

20. A glass syringe barrel, comprising:
   a top end through which a liquid can be ejected;
   a bottom end into which a plunger stopper can be pushed;
   a longitudinal axis $L_{barrel}$ through the top and bottom ends; and
   a cone region having a first end that corresponds to the top end and a second end, the cone region has a length $l_1$ and has an outer diameter $d_1$ at the second end;
   a shoulder region having a first end that is adjacent to the second end of the cone region and a second end, wherein the shoulder region has an outer contour that comprises a concave and substantially circular arc-shaped area $c_1$ with an outer radius $r_1$ beginning below the second end of the cone region and a convex and substantially circular arc-shaped area $c_2$ with an outer radius $r_2$ beginning above the second end of the shoulder region;

a body region having a first end that is adjacent to the second end of the shoulder region and a second end that corresponds to the bottom end, wherein the body region has an outer diameter $d_2$ and a glass thickness $n_2$, wherein $r_1$ is in a range from 0.5 to 3 mm; and a Luer cone breaking resistance that is at least 50 N for a 1% quantile and/or at least 145 N for a 50% quantile, wherein, if an outer surface of the body region is placed on a plane horizontal substrate, within any given cross-section of the glass syringe barrel that is located in a plane centrically located in the glass syringe barrel and comprising the longitudinal axis $L_{barrel}$ of the glass syringe barrel, a first function $f(x)$ defines a vertical distance between the substrate and the outer surface at a given position x, $k(x)=|f''(x)/[1+f'(x)^2]^{3/2}|$ defines an absolute value of the curvature of $f(x)$ at a given position x, and in an interval between $x=P_1$ and $x=P_2$ for any concave curvature in the interval a minimum value for $(1/k(x))/n_2^2$ is at least 0.5 mm$^{-1}$, wherein $P_1$ defines the x-position at which the outer diameter of the glass syringe barrel (100) is 0.95×$d_2$ and $P_2$ is $P_1+3\times n_2$.

21. A glass syringe barrel, comprising:
a top end through which a liquid can be ejected;
a bottom end into which a plunger stopper can be pushed;
a longitudinal axis $L_{barrel}$ through the top and bottom ends; and
a cone region having a first end that corresponds to the top end and a second end, the cone region has a length $l_1$ and has an outer diameter $d_1$ at the second end;
a shoulder region having a first end that is adjacent to the second end of the cone region and a second end, wherein the shoulder region has an outer contour that comprises a concave and substantially circular arc-shaped area $c_1$ with an outer radius $r_1$ beginning below the second end of the cone region and a convex and substantially circular arc-shaped area $c_2$ with an outer radius $r_2$ beginning above the second end of the shoulder region;
a body region having a first end that is adjacent to the second end of the shoulder region and a second end that corresponds to the bottom end, wherein the body region has an outer diameter $d_2$ and a glass thickness $n_2$, wherein $r_1$ is in a range from 0.5 to 3 mm; and
a Luer cone breaking resistance that is at least 50 N for a 1% quantile and/or at least 145 N for a 50% quantile,
wherein $n_s$ is the glass thickness in the shoulder region, measured at the point of the inner shoulder surface at which the surface for the first time forms an angle of 30° with longitudinal axis $L_{barrel}$, and wherein $n_s$ is in the range from 1.2 to 2 mm.

* * * * *